United States Patent [19]
Welter et al.

[11] Patent Number: 6,057,087
[45] Date of Patent: May 2, 2000

[54] PHOTOGRAPHIC ELEMENT CONTAINING YELLOW COUPLER

[75] Inventors: Thomas R. Welter, Webster; James H. Reynolds, Rocheste, both of N.Y.

[73] Assignee: Eastman Kodak Company, Rochester, N.Y.

[21] Appl. No.: 09/069,435

[22] Filed: Apr. 29, 1998

[51] Int. Cl.[7] .............................. G03C 1/08; G03C 7/26; G03C 7/32
[52] U.S. Cl. ...................... 430/557; 430/556; 430/388; 430/389
[58] Field of Search .................... 430/388, 389, 430/556, 557

[56] References Cited

U.S. PATENT DOCUMENTS

| | | | |
|---|---|---|---|
| 3,933,500 | 1/1976 | Shiba et al. | 430/543 |
| 5,312,726 | 5/1994 | Mihayashi et al. | 430/557 |
| 5,314,797 | 5/1994 | Yoshioka et al. | 430/546 |
| 5,352,572 | 10/1994 | Seto et al. | 430/557 |
| 5,674,667 | 10/1997 | Clark et al. | |

FOREIGN PATENT DOCUMENTS

| | | |
|---|---|---|
| 2109P98 | 2/1991 | Japan . |
| 5005974 | 1/1993 | Japan . |

*Primary Examiner*—Geraldine Letscher
*Attorney, Agent, or Firm*—Arthur E. Kluegel

[57] ABSTRACT

Disclosed is a photographic element comprising a silver halide emulsion layer having associated therewith a dye-forming coupler having Formula 1

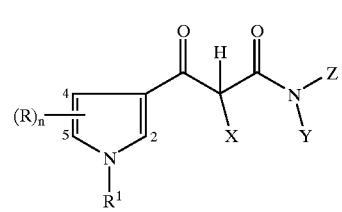

wherein:

X is hydrogen or a coupling-off group, and Y and Z are independently selected hydrogen or a substituent;

$R^1$ is a substituent; and each R is an independently selected substituent with at least one R substituent located in the 2- or 5-position, and n is 1 to 3;

provided that substituents may join to form a ring.

22 Claims, No Drawings

PHOTOGRAPHIC ELEMENT CONTAINING YELLOW COUPLER

FIELD OF THE INVENTION

This invention relates to a photographic element containing a silver halide emulsion layer having associated therewith a dye forming coupler based on a substituted 3-pyrroloylacetamide compound.

BACKGROUND OF THE INVENTION

Conventional color photographic images are formed via a chromogenic development process. After exposure of a color photographic element, the object scene is stored as a composite of red, green and blue silver halide latent images. During the color development process, these silver halide latent images are reductively developed, and an oxidation product of this development reacts with cyan, magenta and yellow dye-forming couplers to provide the desired subtractive primary color images. The composite dye image is then formed by the superpositioning of the cyan, magenta and yellow dye images to afford a reproduction of the original scene. The controlled conversion of silver halide latent image to color dye image is the goal of color photographic chemistry. The yield of dye color density from each unit of silver halide developed is a measure of coupler activity. The higher the activity of a coupler the less silver halide is needed to allow effective image formation. The reduction in the amount of silver halide used in a photographic systems can lead to improved photographic image reproduction, lower cost photographic products, and less potential environmental damage from development processes. Coupler activity, as defined herein, is composed of two prime factors: (1) the efficiency of the dye formation process, i.e., the chemistry converting coupler to dye, and (2) the light absorption properties of the chromogenically formed dye, i.e., the dye's spectral bandshape and extinction. Improvements in dye extinction can lead to desirable improvements in coupler activity and thereby to silver halide reductions.

Two further important features of photographic reproductions are their color fidelity and their image stabilities. To efficiently reproduce a wide gamut of hues, the dyes comprising the color image must exhibit relatively sharp cutting spectral curves. Additionally, the dyes' spectral response curves must be carefully placed, i.e., have a well positioned maximum absorption and curve shape, to afford the best possible color reproduction.

Color photographic images slowly degrade when stored under ambient conditions. Pictures held in the dark, that is, stored in albums, boxes or slide trays and not exposed to direct light, degrade primarily via hydrolytic mechanisms. Images exposed to light fade both via the hydrolytic mechanisms as well as via photochemical processes. The stability of a color image is clearly dependent upon the stabilities of its component dyes. It is apparent from these considerations that the hydrolytic stability of photographic dyes is of primary importance to image stability. The destruction of photographic dyes may be catalyzed by either acids or bases; dyes that are robustly stable to various hydrolytic conditions will provide more stable photographic images.

Various efforts have been undertaken to provide a yellow dye-forming coupler that exhibits an improved combination of activity and image stability. A new class of photographic yellow couplers was recently patented by Bernard Clark, et al. in U.S. Pat. No. 5,674,667. This patent discloses a novel class of pyrroloyl-acetanilide couplers that exhibit a combination of improved dye contrast and dye stability. These characteristics were found to be comparable or superior to the couplers used in commercial photographic products. Comparative examples of this art are identified hereinafter.

In spite of the efforts to obtain improved yellow couplers, there is still a need for improved yellow couplers for which the stability of the image dye is enhanced.

SUMMARY OF THE INVENTION

The invention provides a photographic element comprising a silver halide emulsion layer having associated therewith a dye-forming coupler having Formula 1

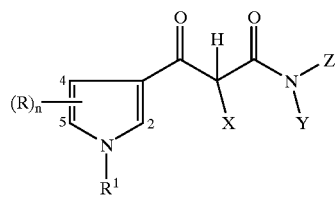

wherein:
   X is hydrogen or a coupling-off group, and Y and Z are independently selected hydrogen or a substituent;
   $R^1$ is hydrogen or a substituent; and
   each R is an independently selected substituent with at least one R substituent located in the 2- or 5-position, and n is 1 to 3;
   provided that substituents may join to form a ring.

The invention also provides a coupler composition, a dye composition, and a process for forming an image.

The invention provides yellow couplers for which the stability of the image dye is enhanced.

DETAILED DESCRIPTION OF THE INVENTION

The invention provides a photographic element comprising a silver halide emulsion layer having associated therewith a dye-forming coupler having Formula 1:

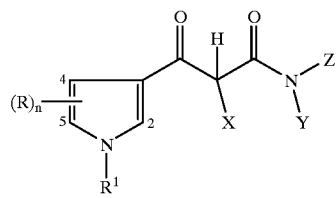

wherein:
   X is hydrogen or a coupling-off group, and Y and Z are independently selected hydrogen or a substituent;
   $R^1$ is hydrogen or a substituent; and
   each R is an independently selected substituent with at least one R substituent located in the 2- or 5-position, and n is 1 to 3;
   provided that substituents may join to form a ring.

As may be observed, the formula contains several variable substituents. The substituent X is bonded to the coupling position and may be hydrogen or any coupling-off group as more fully described hereinafter. Such groups are capable of being displaced during oxidative coupling and are typically halogen or a group bonded to the coupling site by a heteroatom such as oxygen, sulfur or nitrogen. Most useful are those employing halogen or a group linked to the coupling site by an atom of oxygen or sulfur or a nitrogen heterocyclic group bonded to the coupling site by a nitrogen atom of the group. Specifically, X is suitably hydrogen, chloro, an N-heterocyclic ring group or a phenyl group bonded to the coupling position through an atom of oxygen or sulfur. Desirably, X is a hydrogen atom, a chlorine atom or an N-heterocyclic, phenoxy, or phenylthio group.

$R^1$ is a substituent. Any substituent bonded through a carbon atom is may commonly be employed. Suitable examples include alkyl and aryl groups as well as heterocyclic aromatic and non-aromatic groups. Specific examples are methyl, ethyl, benzyl, phenyl, dodecyl, tetradecyl, hexadecyl, phenylethyl, and pyridyl groups. Methyl, benzyl and phenyl are conveniently used.

The various R groups may be any substituent group, such as a carbon linked substituent, as defined hereinafter. Examples include alkyl, acyl, halogen, carboxyl, alkoxy, carbonamido, carbamoyl, heterocyclic, and aryl groups such as methyl, ethyl, isopropyl, trifluoromethyl, t-butyl, methoxy, methylacetamido, naphthyl, and phenyl groups. One of these substituents must be present in position 2 or 5 of the pyrrole ring. The best dye stability is obtained under these circumstances. It further appears that even further improvement in dye stability is obtained if n is 2 or 3.

Y and Z may be independently selected hydrogen or substituent groups. Suitable substituents include any alkyl, aryl and hetero groups. Examples include methyl ethyl, phenyl, cyclohexyl, and naphthyl. Typically, Y is a substituent and Z is hydrogen. Most commonly Y is a phenyl group and Z is hydrogen. When Y is a phenyl group it desirably has the formula:

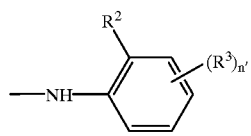

In the above formula, $R^2$ may be hydrogen or any substituent such as halogen, alkoxy, acyl, amido, etc. Suitable examples are alkoxy such as methoxy, ethoxy, propoxy and isopropoxy and halogen such as bromine or chlorine. $R^3$ may be any substituent, particularly one containing an electron withdrawing group (Hammett's Sigma value >0 (location relative to the anilino nitrogen)) such as $-SO_2R^4$, $-SO_2NR^4$, $-CO_2R^4$, $-CONR^4$, $-COR^4$, $-NR^4COR^4$, $-NR^4SO_2R^4$ wherein each $R^4$ is independently H or a substituent. The R4 substituent may be interrupted by one or more heteroatoms or groups. Typically, $R^3$ contains $-SO_2R^4$, $-SO_2NHR^4$, or $-CO_2R^4$. $R^3$ most typically contains the electron withdrawing group bonded directly to the coupler residue. R4 may be hydrogen or any substituent such as an alkyl or aryl group, particularly an alkyl group of 4 to 20 carbon atoms. The variable n' may be 0–4, suitably 0–3 and typically 0–2. Commonly, the phenyl ring bears a ballast substituent, as described more fully hereinafter. A particularly useful example is shown in the following formula:

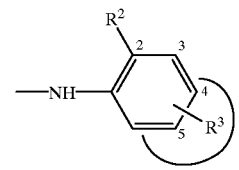

$R^2$ is a chloro or alkoxy group. The arc is intended to indicate that at least one $R^3$ substituent is present in the 4- or 5- position of the formula. The $R^3$ substituent is linked to the residue of the coupler by one of the indicated electron withdrawing groups as described for F-3 and contains a ballast group as described hereinafter.

One embodiment of a coupler useful in the invention is formula A:

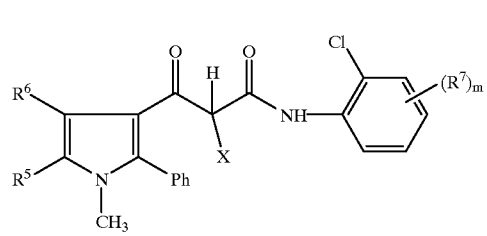

in which $R^5$ and $R^6$ are independently selected hydrogen or substituents, suitably hydrogen or alkyl or aryl groups;

X is hydrogen or a coupling-off group;

each $R^7$ is a substituent and m is 0–4;

provided that substituents may join to form a ring.

A second embodiment is shown by formula B:

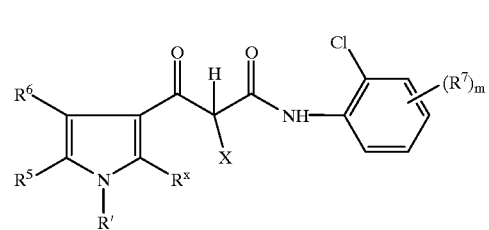

in which $R^5$ and $R^6$ are independently selected hydrogen or substituents, suitably hydrogen or alkyl or aryl groups;

X is hydrogen or a coupling-off group;

R' and $R^x$ are independently selected substituents such as alkyl or aryl groups;

each $R^7$ is a substituent and m is 0–4;

provided that substituents may join to form a ring.

In addition to producing image dyes that exhibit enhanced dye stability, embodiments of the invention also exhibit desirable high extinctions, high coupling activity, and advantageous dye hue.

The following are examples of couplers of the invention.

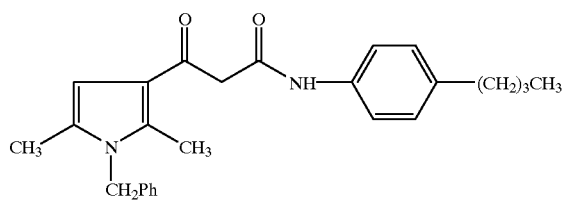
C-1
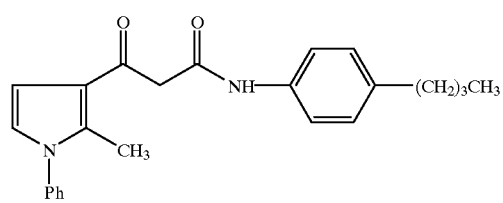
C-2
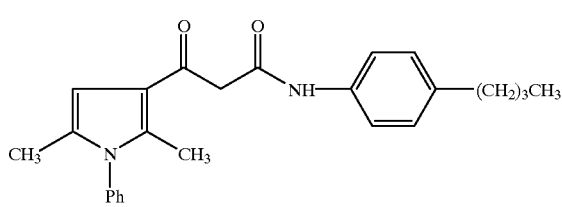
C-3
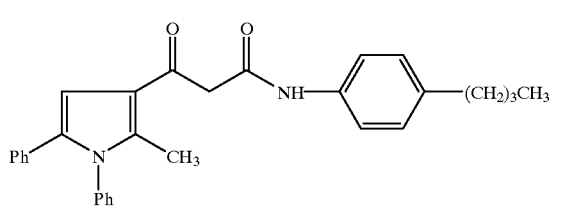
C-4
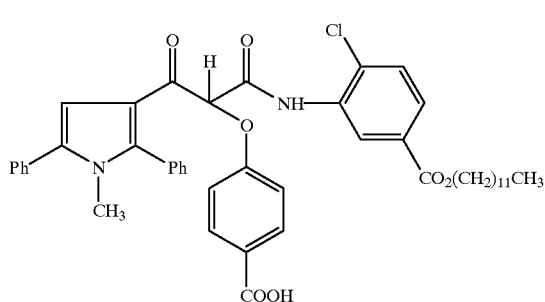
C-5
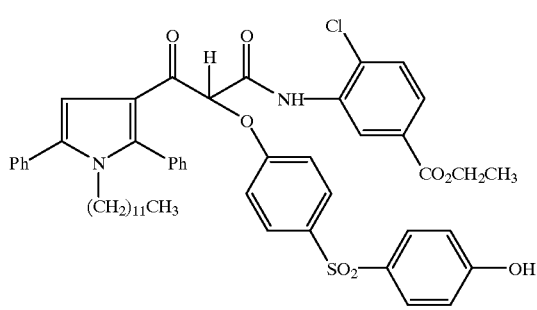
C-6

-continued
C-7
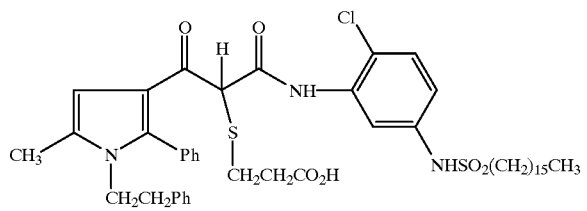
C-8
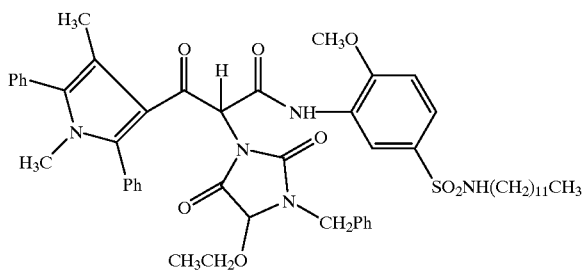
C-9
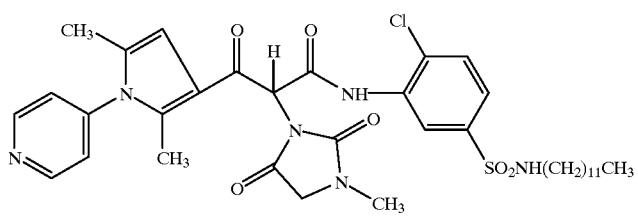
C-10
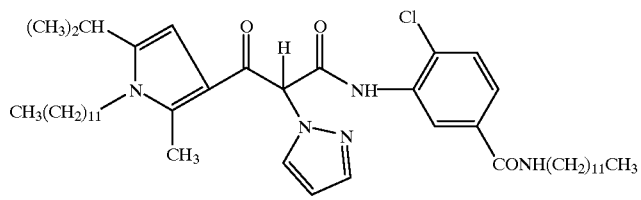
C-11
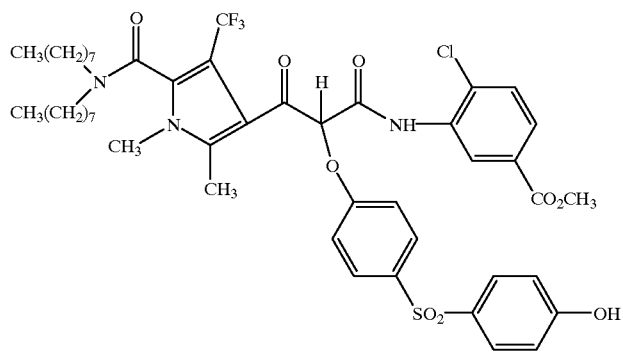
C-12
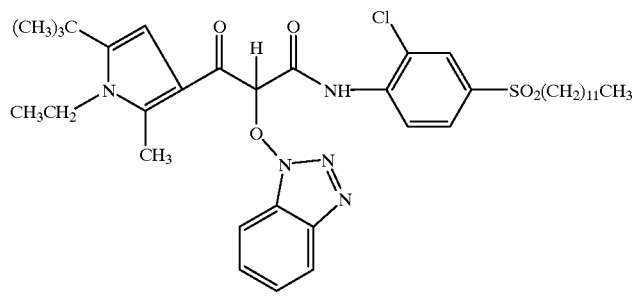

C-13
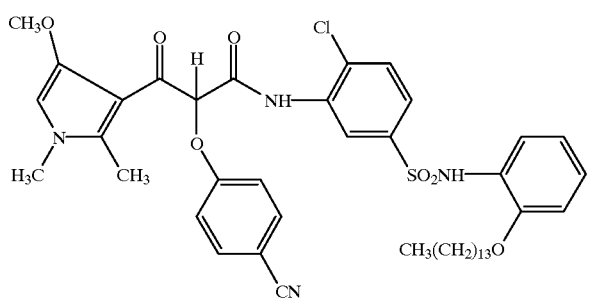
C-14
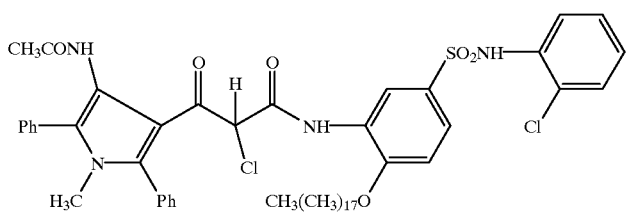
C-15
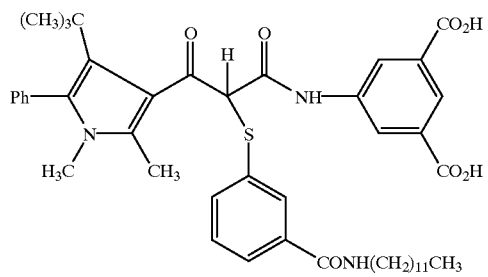
C-16
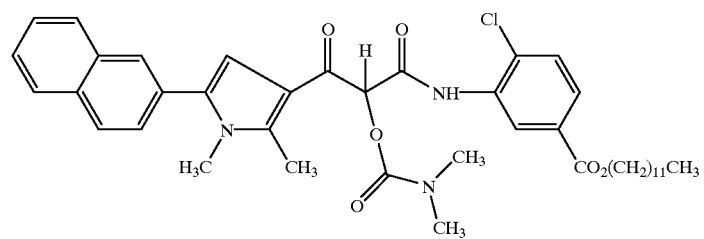
C-17
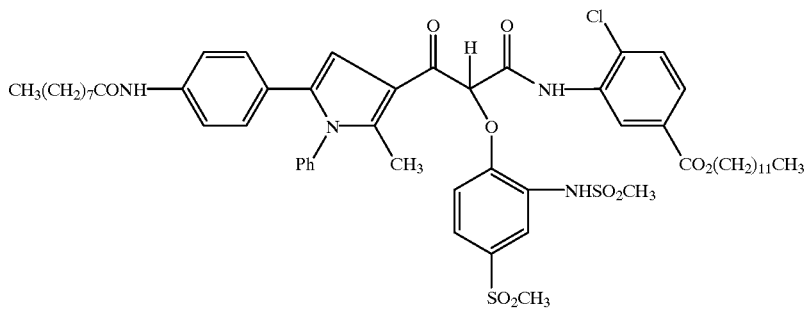

-continued
C-18
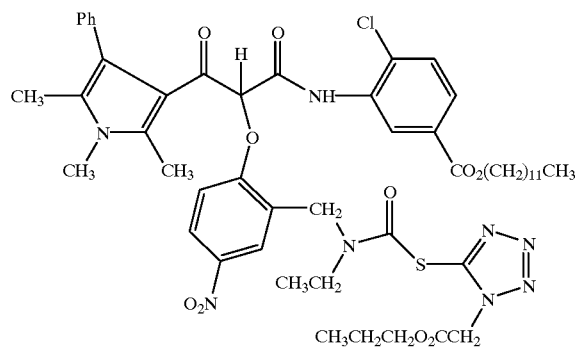
C-19
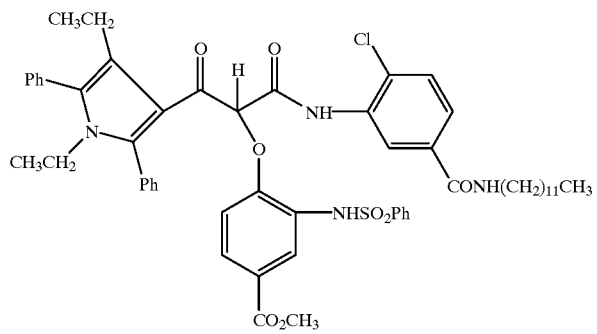
C-20
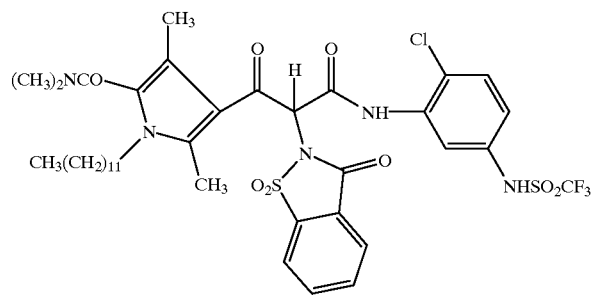
C-21
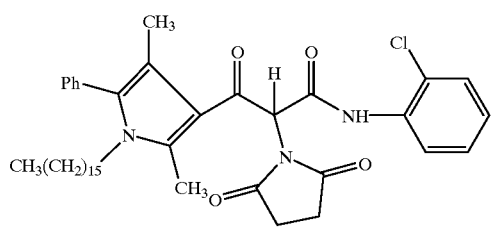
C-22
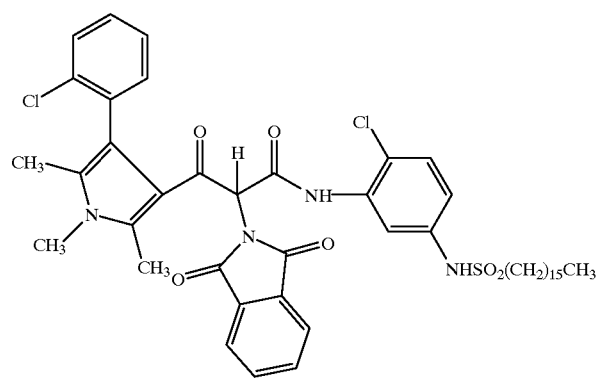

-continued
C-23
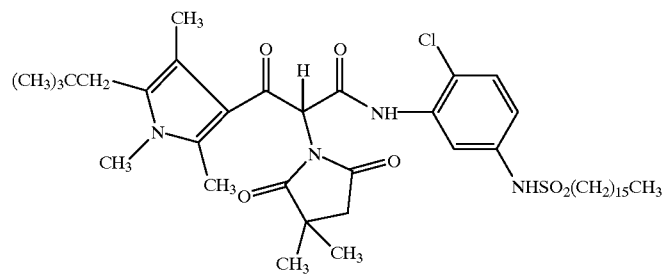
C-24
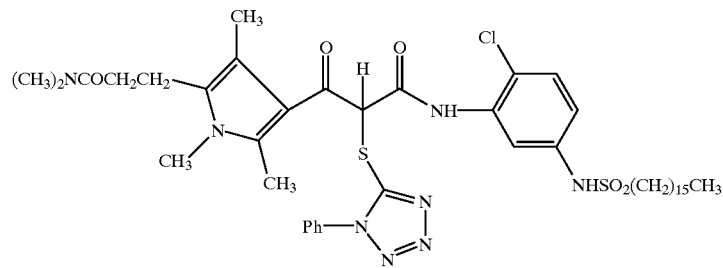
C-25
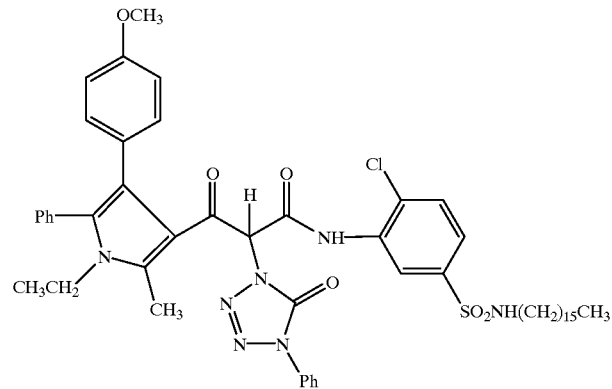
C-26
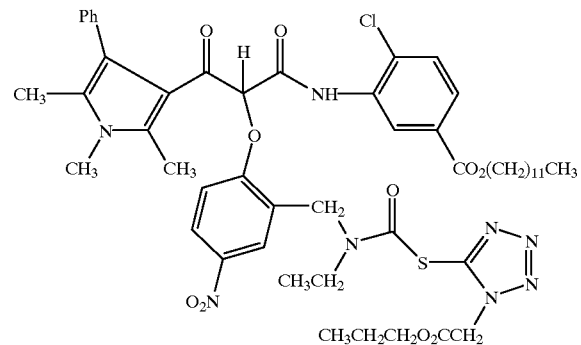
C-27
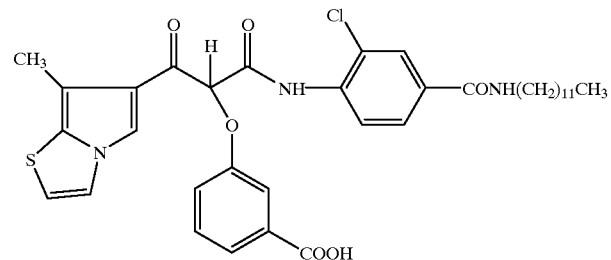

-continued
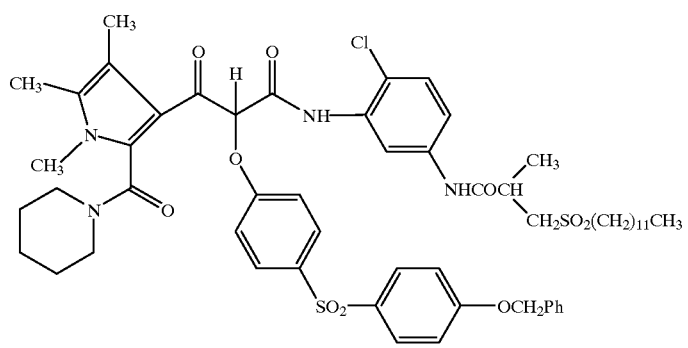
C-28
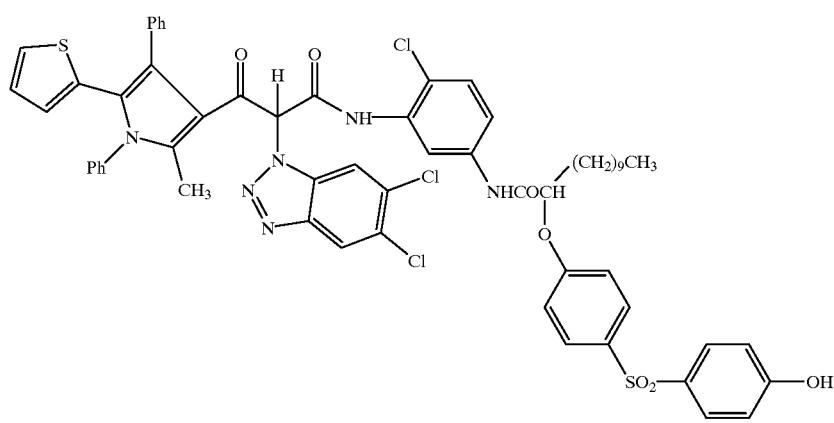
C-29
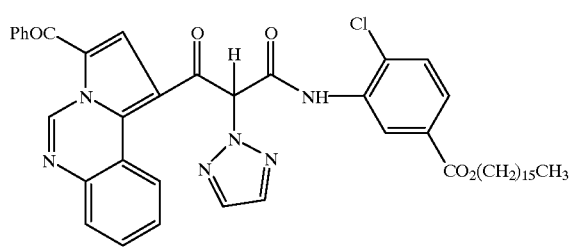
C-30
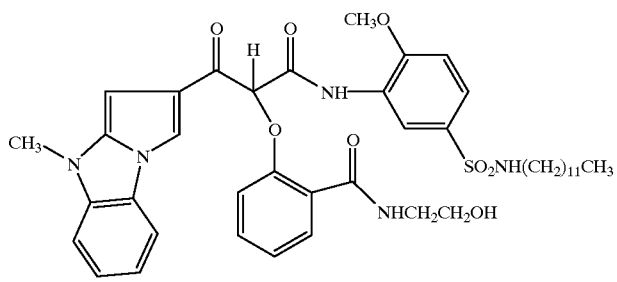
C-31
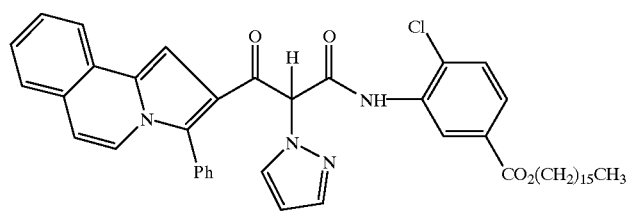
C-32

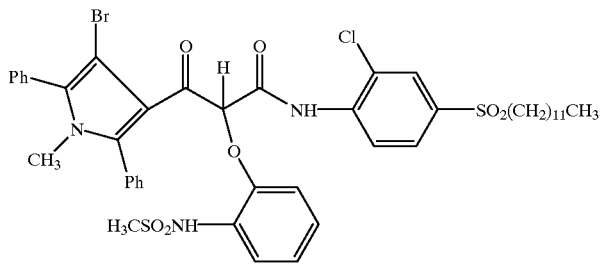

C-33

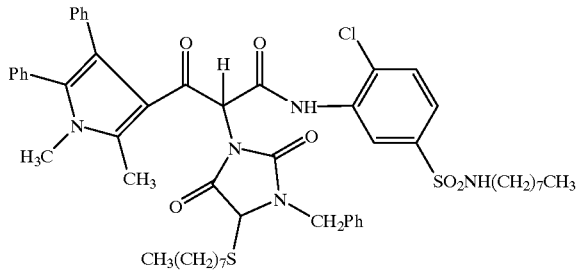

C-34

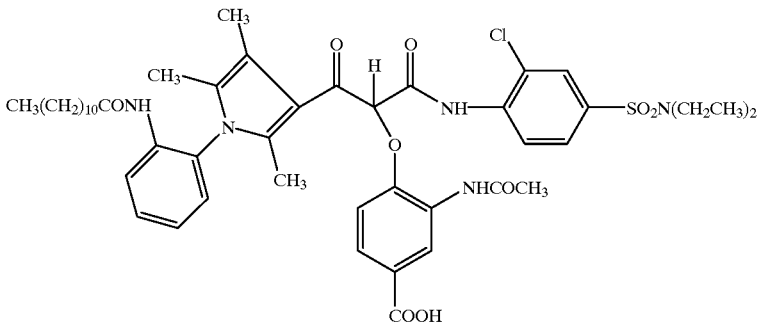

C-35

The dyes of the invention are derived from the coupler of the invention. Thus the dyes comprise the coupling product of a coupler of the invention and an oxidized color developer. Such developers are typically para-phenylenediamine compounds which are well-known in the art. Such a dye is represented by the formula:

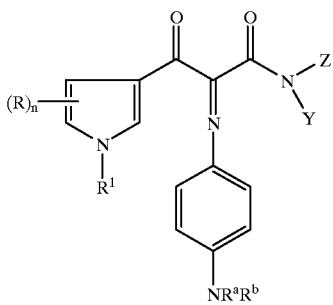

wherein:

$R^a$ and $R^b$ are each independently selected hydrogen or a substituent and the remaining variables are as defined for formula 1.

The imaging process of the invention is any process for forming an image in an element of the invention using a color developer. If desired it may be a reversal element in which the image is first developed with a non-color developer followed by uniform fogging and development with a color developer. The element may also be a color negative provided on transparent film designed for optical printing or one on a transparent or reflective support designed for forming a positive image to be directly or indirectly viewed.

Unless otherwise specifically stated, the term substituent means any group or atom other than hydrogen bonded to the remainder of a molecule. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for photographic utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2, 4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecyl-phenylcarbonylamino, p-tolylcarbonylamino, N-methylureido, N,N-dimethylureido, N-methyl-N-dodecylureido, N-hexadecylureiedo, N,N-dioctadecylurcido, N,N-dioctyl-N'-ethylureido, N-phenylureido, N,N-diphenylureido, N-phenyl-N-p-tolylureido, N-(ni-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphcnylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

The materials of the invention can be used in any of the ways and in any of the combinations known in the art. Typically, the invention materials are incorporated in a silver halide emulsion and the emulsion coated as a layer on a support to form part of a photographic element. Alternatively, unless provided otherwise, they can be incorporated at a location adjacent to the silver halide emulsion layer where, during development, they will be in reactive association with development products such as oxidized color developing agent. Thus, as used herein, the term "associated" signifies that the compound is in the silver halide emulsion layer or in an adjacent location where, during processing, it is capable of reacting with silver halide development products.

To control the migration of various components, it may be desirable to include a high molecular weight hydrophobe or "ballast" group in coupler molecules. Representative ballast groups include substituted or unsubstituted alkyl or aryl groups containing 8 to 48 carbon atoms. Representative substituents on such groups include alkyl, aryl, alkoxy, aryloxy, alkylthio, hydroxy, halogen, alkoxycarbonyl, aryloxcarbonyl, carboxy, acyl, acyloxy, amino, anilino, carbonamido, carbamoyl, alkylsulfonyl, arylsulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire PO1O 7DQ, ENGLAND, and as described in Hatsumi Kyoukai Koukai Gihou No. 94-6023, published Mar. 15, 1994, available from the Japanese Patent Office, the contents of which are incorporated herein by reference. When it is desired to employ the inventive materials in a small format film, *Research Disclosure*, June 1994, Item 36230, provides suitable embodiments.

In the following discussion of suitable materials for use in the emulsions and elements of this invention, reference will be made to *Research Disclosure*, September 1996, Item 38957, available as described above, which is referred to herein by the term "Research Disclosure". The contents of the Research Disclosure, including the patents and publications referenced therein, are incorporated herein by reference, and the Sections hereafter referred to are Sections of the Research Disclosure.

Except as provided, the silver halide emulsion containing elements employed in this invention can be either negative-working or positive-working as indicated by the type of processing instructions (i.e. color negative, reversal, or direct positive processing) provided with the element. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Suitable methods for incorporating couplers and dyes, including dispersions in organic solvents, are described in Section X(E). Scan facilitating is described in Section XIV. Supports, exposure, development systems, and processing methods and agents are described in Sections XV to XX. The information contained in the September 1994 *Research Disclosure*, Item No. 36544 referenced above, is updated in the September 1996 *Research Disclosure*, Item No. 38957. Certain desirable photographic elements and processing steps, including those useful in conjunction with color reflective prints, are described in *Research Disclosure*, Item 37038, February 1995.

Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction and the like.

The presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in UK. Patents and published application Nos. 1,466,728, 1,531,927, 1,533,039, 2,006,755A and 2,017,704A, the disclosures of which are incorporated herein by reference.

Image dye-forming couplers may be included in the element such as couplers that form cyan dyes upon reaction with oxidized color developing agents which are described in such representative patents and publications as: "Farbkuppler-eine Literature Ubersicht," published in Agfa Mitteilungen, Band III, pp. 156–175 (1961) as well as in U.S. Pat. Nos. 2,367,531; 2,423,730; 2,474,293; 2,772,162; 2,895,826; 3,002,836; 3,034,892; 3,041,236; 4,333,999; 4,746,602; 4,753,871; 4,770,988; 4,775,616; 4,818,667; 4,818,672; 4,822,729; 4,839,267; 4,840,883; 4,849,328; 4,865,961; 4,873,183; 4,883,746; 4,900,656; 4,904,575; 4,916,051; 4,921,783; 4,923,791; 4,950,585; 4,971,898; 4,990,436; 4,996,139; 5,008,180; 5,015,565; 5,011,765; 5,011,766; 5,017,467; 5,045,442; 5,051,347; 5,061,613; 5,071,737; 5,075,207; 5,091,297; 5,094,938; 5,104,783; 5,178,993; 5,813,729; 5,187,057; 5,192,651; 5,200,305 5,202,224; 5,206,130; 5,208,141; 5,210,011; 5,215,871; 5,223,386; 5,227,287; 5,256,526; 5,258,270; 5,272,051; 5,306,610; 5,326,682; 5,366,856; 5,378,596; 5,380,638; 5,382,502; 5,384,236; 5,397,691; 5,415,990; 5,434,034; 5,441,863; EPO 0 246 616; EPO 0 250 201; EPO 0 271 323; EPO 0 295 632; EPO 0 307 927; EPO 0 333 185; EPO 0 378 898; EPO 0 389 817; EPO 0 487 111; EPO 0 488 248; EPO 0 539 034; EPO 0 545 300; EPO 0 556 700; EPO 0 556 777; EPO 0 556 858; EPO 0 569 979; EPO 0 608 133; EPO 0 636 936; EPO 0 651 286; EPO 0 690 344; German OLS 4,026,903; German OLS 3,624,777 and German OLS 3,823,049. Typically such couplers are phenols, naphthols, or pyrazoloazoles.

Couplers that form magenta dyes upon reaction with oxidized color developing agent are described in such representative patents and publications as: "Farbkuppler-eine Literature Ubersicht," published in Agfa Mitteilungen, Band III, pp. 126–156 (1961) as well as U.S. Pat. Nos. 2,311,082 and 2,369,489; 2,343,701; 2,600,788; 2,908,573; 3,062,653; 3,152,896; 3,519,429; 3,758,309; 3,935,015; 4,540,654; 4,745,052; 4,762,775; 4,791,052; 4,812,576; 4,835,094; 4,840,877; 4,845,022; 4,853,319; 4,868,099; 4,865,960; 4,871,652; 4,876,182; 4,892,805; 4,900,657; 4,910,124; 4,914,013; 4,921,968; 4,929,540; 4,933,465; 4,942,116; 4,942,117; 4,942,118; 4,959,480; 4,968,594; 4,988,614; 4,992,361; 5,002,864; 5,021,325; 5,066,575; 5,068,171; 5,071,739; 5,100,772; 5,110,942; 5,116,990; 5,118,812; 5,134,059; 5,155,016; 5,183,728; 5,234,805; 5,235,058; 5,250,400; 5,254,446; 5,262,292; 5,300,407; 5,302,496; 5,336,593; 5,350,667; 5,395,968; 5,354,826; 5,358,829; 5,368,998; 5,378,587; 5,409,808; 5,411,841; 5,418,123; 5,424,179; EPO 0 257 854; EPO 0 284 240; EPO 0 341 204; EPO 347,235; EPO 365,252; EPO 0 422 595; EPO 0 428 899; EPO 0 428 902; EPO 0 459 331; EPO 0 467 327; EPO 0 476 949; EPO 0 487 081; EPO 0 489 333; EPO 0 512 304; EPO 0 515 128; EPO 0 534 703; EPO 0 554 778; EPO 0 558 145; EPO 0 571 959; EPO 0 583 832; EPO 0 583 834; EPO 0 584 793; EPO 0 602 748; EPO 0 602 749; EPO 0 605 918; EPO 0 622 672; EPO 0 622 673; EPO 0 629 912; EPO 0 646 841, EPO 0 656 561; EPO 0 660 177; EPO 0 686 872; WO 90/10253; WO 92/09010; WO 92/10788; WO 92/12464; WO 93/01523; WO 93/02392; WO 93/02393; WO 93/07534; UK Application 2,244,053; Japanese Application 03192–350; German OLS 3,624,103; German OLS 3,912,265; and German OLS 40 08 067. Typically such couplers are pyrazolones, pyrazoloazoles, or pyrazolobenzimidazoles that form magenta dyes upon reaction with oxidized color developing agents.

Couplers that form yellow dyes upon reaction with oxidized color developing agent are described in such representative patents and publications as: "Farbkuppler-eine Literature Ubersicht," published in Agfa Mitteilungen; Band III; pp. 112–126 (1961); as well as U.S. Pat. Nos. 2,298,443; 2,407,210; 2,875,057; 3,048,194; 3,265,506; 3,447,928; 4,022,620; 4,443,536; 4,758,501; 4,791,050; 4,824,771; 4,824,773; 4,855,222; 4,978,605; 4,992,360; 4,994,361; 5,021,333; 5,053,325; 5,066,574; 5,066,576; 5,100,773; 5,118,599; 5,143,823; 5,187,055; 5,190,848; 5,213,958; 5,215,877; 5,215,878; 5,217,857; 5,219,716; 5,238,803; 5,283,166; 5,294,531; 5,306,609; 5,328,818; 5,336,591; 5,338,654; 5,358,835; 5,358,838; 5,360,713; 5,362,617; 5,382,506; 5,389,504; 5,399,474;. 5,405,737; 5,411,848; 5,427,898; EPO 0 327 976; EPO 0 296 793; EPO 0 365 282; EPO 0 379 309; EPO 0 415 375; EPO 0 437 818; EPO 0 447 969; EPO 0 542 463; EPO 0 568 037; EPO 0 568 196; EPO 0 568 777; EPO 0 570 006; EPO 0 573 761; EPO 0 608 956; EPO 0 608 957; and EPO 0 628 865. Such couplers are typically open chain ketomethylene compounds.

Couplers that form colorless products upon reaction with oxidized color developing agent are described in such representative patents as: UK. 861,138; U.S. Pat. Nos. 3,632, 345; 3,928,041; 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or maminophenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3-position may be employed. Couplers of this type are described, for example, in U.S. Pat. Nos. 5,026,628, 5,151, 343, and 5,234,800.

It may be useful to use a combination of couplers any of which may contain known ballasts or coupling-off groups such as those described in U.S. Pat. Nos. 4,301,235; 4,853, 319 and 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with masking couplers such as those described in EP 213.490; Japanese Published Application 58-172,647; U.S. Patent Nos. 2,983, 608; 4,070,191; and 4,273,861; German Applications DE 2,706,117 and DE 2,643,965; UK. Patent 1,530,272; and Japanese Application 58-113935. The masking couplers may be shifted or blocked, if desired.

Typically, couplers are incorporated in a silver halide emulsion layer in a mole ratio to silver of 0.1 to 1.0 and generally 0.1 to 0.5. Usually the couplers are dispersed in a high-boiling organic solvent in a weight ratio of solvent to coupler of 0.1 to 10.0, typically 0.1 to 2.0 and usually 0.1 to 0.6, although dispersions without high-boiling solvent are sometimes employed.

The invention materials may be used in association with materials that release Photographically Useful Groups (PUGS) that accelerate or otherwise modify the processing steps e.g. of bleaching or fixing to improve the quality of the image. Bleach accelerator releasing couplers such as those described in EP 193,389; EP 301,477; U.S. Pat. Nos. 4,163, 669; 4,865,956; and 4,923,784, may be useful. Also contemplated is use of the compositions in association with nucleating agents, development accelerators or their precursors (UK. Patent 2,097,140; UK. Patent 2,131,188); electron transfer agents (U.S. Pat. Nos. 4,859,578; 4,912,025); anti-fogging and anti color-mixing agents such as derivatives of hydroquinones, aminophenols, amines, gallic acid; catechol; ascorbic acid; hydrazides; sulfonamidophenols; and non color-forming couplers.

The invention materials may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543, 323.) Also, the compositions may be blocked or coated in protected form as described, for example, in Japanese Application 61/258,249 or U.S. Pat. No. 5,019,492.

The invention materials may further be used in combination with image-modifying compounds that release PUGS such as "Developer Inhibitor-Releasing" compounds (DIR's). DIR's useful in conjunction with the compositions of the invention are known in the art and examples are described in U.S. Pat. Nos. 3,137,578; 3,148,022; 3,148, 062; 3,227,554; 3,384,657; 3,379,529; 3,615,506; 3,617, 291; 3,620,746; 3,701,783; 3,733,201; 4,049,455; 4,095, 984; 4,126,459; 4,149,886; 4,150,228; 4,211,562; 4,248, 962; 4,259,437; 4,362,878; 4,409,323; 4,477,563; 4,782, 012; 4,962,018; 4,500,634; 4,579,816; 4,607,004; 4,618, 571; 4,678,739; 4,746,600; 4,746,601; 4,791,049; 4,857, 447; 4,865,959; 4,880,342; 4,886,736; 4,937,179; 4,946, 767; 4,948,716; 4,952,485; 4,956,269; 4,959,299; 4,966, 835; 4,985,336 as well as in patent publications GB 1,560, 240; GB 2,007,662; GB 2,032,914; GB 2,099,167; DE 2,842,063, DE 2,937,127; DE 3,636,824; DE 3,644,416 as well as the following European Patent Publications: 272, 573; 335,319; 336,411; 346, 899; 362, 870; 365,252; 365, 346; 373,382; 376,212; 377,463; 378,236; 384,670; 396, 486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

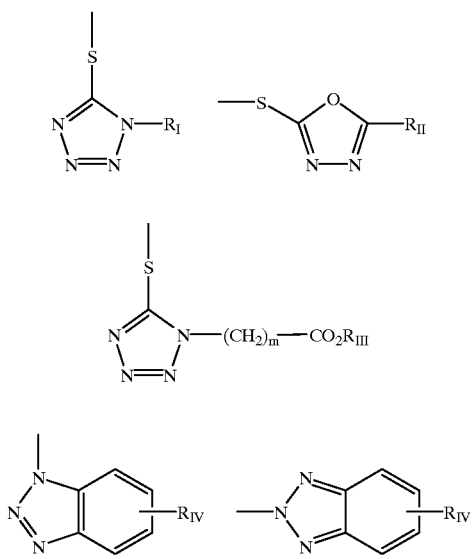

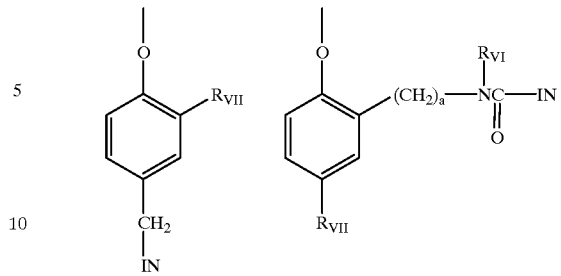

wherein IN is the inhibitor moiety, $R_{VII}$ is selected from the group consisting of nitro, cyano, alkylsulfonyl; sulfamoyl; and sulfonamido groups; a is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

The timing or linking groups may also function by electron transfer down an unconjugated chain. Linking groups are known in the art under various names. Often they have been referred to as groups capable of utilizing a hemiacetal or iminoketal cleavage reaction or as groups capable of utilizing a cleavage reaction due to ester hydrolysis such as U.S. Pat. No. 4,546,073. This electron transfer down an unconjugated chain typically results in a relatively fast decomposition and the production of carbon dioxide, formaldehyde, or other low molecular weight by-products. The groups are exemplified in EP 464,612, EP 523,451, U.S. Pat. No. 4,146,396, Japanese Kokai 60-249148 and 60-249149.

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $Rif_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

A compound such as a coupler may release a PUG directly upon reaction of the compound during processing, or indirectly through a timing or linking group. A timing group produces the time-delayed release of the PUG such groups using an intramolecular nucleophilic substitution reaction (U.S. Pat. No. 4,248,962); groups utilizing an electron transfer reaction along a conjugated system (U.S. Pat. Nos. 4,409,323; 4,421,845; 4,861,701, Japanese Applications 57-188035; 58-98728; 58-209736; 58-209738); groups that function as a coupler or reducing agent after the coupler reaction (U.S. 4,438,193; U.S. 4,618,571) and groups that combine the features describe above. It is typical that the timing group is of one of the formulas:

Suitable developer inhibitor-releasing couplers for use in the present invention include, but are not limited to, the following:

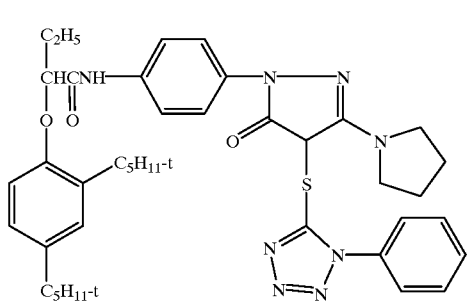

D1

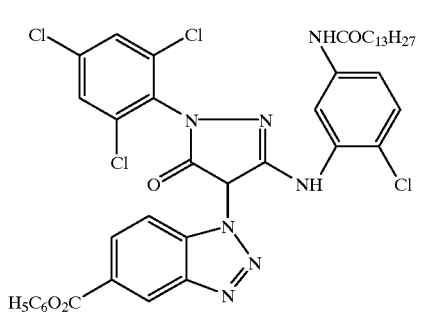

D2

D3 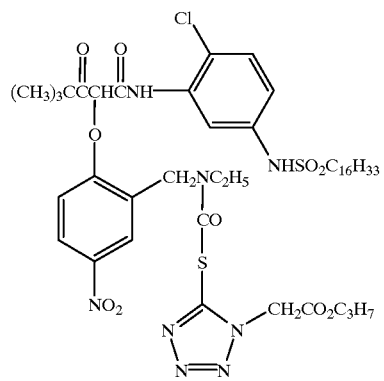
D4 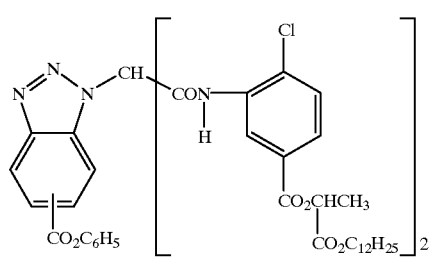
D5 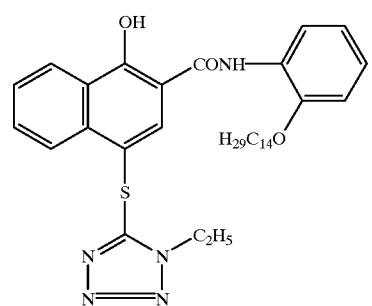
D6 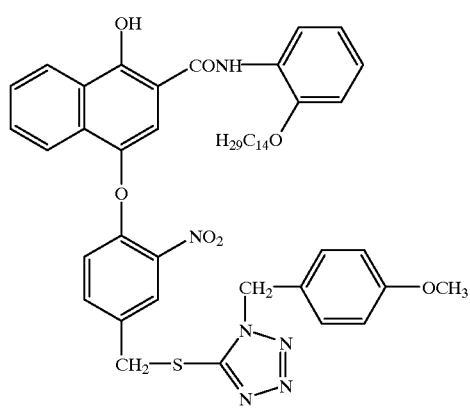
D7 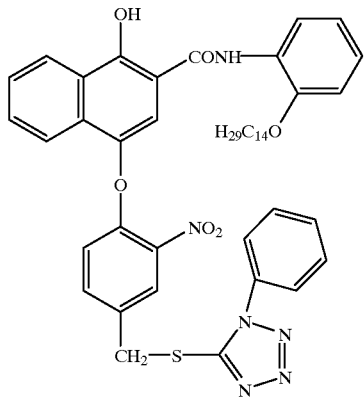
D8 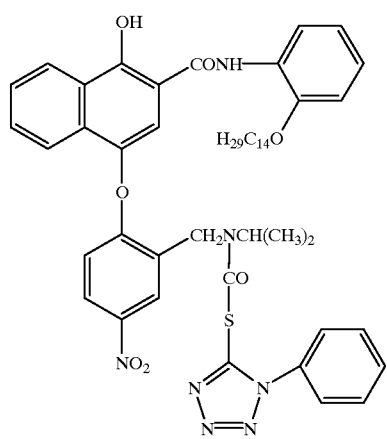
D9 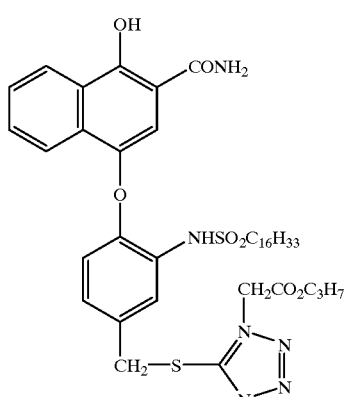

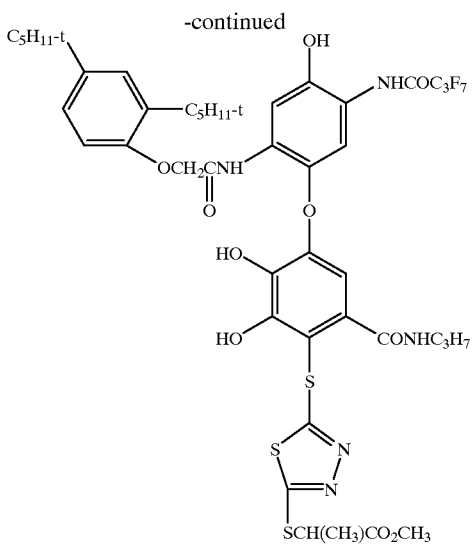

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; on a support with reduced oxygen permeability (EP 553,339); with epoxy solvents (EP 164,961); with nickel complex stabilizers (U.S. Pat. Nos. 4,346,165; 4,540,653 and 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90-072,632; 90-072,633; 90-072, 634; 90-077,822; 90-078,229; 90-078,230; 90-079,336; 90-079,337; 90-079,338; 90-079,690; 90-079,691; 90-080, 487; 90-080,488; 90-080,489; 90-080,490; 90-080,491; 90-080,492; 90-080,494; 90-085,928; 90-086,669; 90-086, 670; 90-087,360; 90-087,361; 90-087,362; 90-087,363; 90-087,364; 90-088,097; 90-093,662; 90-093,663; 90-093, 664; 90-093,665; 90-093,666; 90-093,668; 90-094,055; 90-094,056; 90-103,409; 83–62,586; 83–09,959.

Conventional radiation-sensitive silver halide emulsions can be employed in the practice of this invention. Such emulsions are illustrated by *Research Disclosure*, Item 38755, September 1996, I. Emulsion grains and their preparation.

Especially useful in this invention are tabular grain silver halide emulsions. Tabular grains are those having two parallel major crystal faces and having an aspect ratio of at least 2. The term "aspect ratio" is the ratio of the equivalent circular diameter (ECD) of a grain major face divided by its thickness (t). Tabular grain emulsions are those in which the tabular grains account for at least 50 percent (preferably at least 70 percent and optimally at least 90 percent) of total grain projected area. Preferred tabular grain emulsions are those in which the average thickness of the tabular grains is less than 0.3 micrometer (preferably thin—that is, less than 0.2 micrometer and most preferably ultrathin—that is, less than 0.07 micrometer). The major faces of the tabular grains can lie in either {111} or {100} crystal planes. The mean ECD of tabular grain emulsions rarely exceeds 10 micrometers and more typically is less than 5 micrometers.

In their most widely used form tabular grain emulsions are high bromide {111} tabular grain emulsions. Such emulsions are illustrated by Kofron et al U.S. Pat. No. 4,439,520, Wilgus et al U.S. Pat. No. 4,434,226, Solberg et al U.S. Pat. No. 4,433,048, Maskasky U.S. Pat. Nos. 4,435, 501, 4,463,087 and 4,173,320, Daubendiek et al U.S. Pat. Nos. 4,414,310 and 4,914,014, Sowinski ct al U.S. Pat. No. 4,656,122, Piggin et al U.S. Pat. Nos. 5,061,616 and 5,061, 609, Tsaur et al U.S. Pat. Nos. 5,147,771, '772, '773, 5,171,659 and 5,252,453, Black et al U.S. Pat. No. 5,219, 720 and 5,334,495, Delton U.S. Pat. Nos. 5,310,644, 5,372, 927 and 5,460,934, Wen U.S. Pat. No. 5,470,698, Fenton et al U.S. Pat. No. 5,476,760, Eshelman et al U.S. Pat. Nos. 5,612,175 and 5,614,359, and Irving et al U.S. Pat. No. 5,667,954.

Ultrathin high bromide {111} tabular grain emulsions are illustrated by Daubendiek et al U.S. Pat. Nos. 4,672,027, 4,693,964, 5,494,789, 5,503,971 and 5,576,168, Antoniades et al U.S. Pat. No. 5,250,403, Olm et al U.S. Pat. No. 5,503,970, Deaton et al U.S. Pat. No. 5,582,965, and Maskasky U.S. Pat. No. 5,667,955.

High bromide {100} tabular grain emulsions are illustrated by Mignot U.S. Pat. Nos. 4,386,156 and 5,386,156.

High chloride {111} tabular grain emulsions are illustrated by Wey U.S. Pat. No. 4,399,215, Wey et al U.S. Pat. No. 4,414,306, Maskasky U.S. Pat. Nos. 4,400,463, 4,713, 323, 5,061,617, 5,178,997, 5,183,732, 5,185,239, 5,399,478 and 5,411,852, and Maskasky et al U.S. Pat. Nos. 5,176,992 and 5,178,998. Ultrathin high chloride {111} tabular grain emulsions are illustrated by Maskasky U.S. Pat. Nos. 5,271, 858 and 5,389,509.

High chloride {100} tabular grain emulsions are illustrated by Maskasky U.S. Pat. Nos. 5,264,337, 5,292,632, 5,275,930 and 5,399,477, House et al U.S. Pat. No. 5,320, 938, Brust et al U.S. Pat. No. 5,314,798, Szajewski et al U.S. Pat. No. 5,356,764, Chang et al U.S. Pat. Nos. 5,413,904 and 5,663,041, Oyamada U.S. Pat. No. 5,593,821, Yamashita et al U.S. Pat. Nos. 5,641,620 and 5,652,088, Saitou et al U.S. Pat. No. 5,652,089, and Oyamada et al U.S. Pat. No. 5,665,530. Ultrathin high chloride {100} tabular grain emulsions can be prepared by nucleation in the presence of iodide, following the teaching of House et al and Chang et al, cited above.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent. Tabular grain emulsions of the latter type are illustrated by Evans et al. U.S. Pat. No. 4,504,570.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye. If desired "Redox Amplification" as described in Research Disclosure XVIIIB(5) may be used.

With negative-working silver halide, the processing step described above provides a negative image. One type of such element, referred to as a color negative film, is designed for image capture. Speed (the sensitivity of the element to low light conditions) is usually critical to obtaining sufficient image in such elements. Such elements are typically silver bromoiodide emulsions coated on a transparent support and may be processed, for example, in known color negative processes such as the Kodak C-41 process as described in The British Journal of Photography Annual of 1988, pages 191–198. if a color negative film element is to be subsequently employed to generate a viewable projection print as for a motion picture, a process such as the Kodak ECN-2 process described in the H-24 Manual available from Eastman Kodak Co. may be employed to provide the color negative image on a transparent support. Color negative development times are typically 3' 15" or less and desirably 90 or even 60 seconds or less.

The photographic element of the invention can be incorporated into exposure structures intended for repeated use or exposure structures intended for limited use, variously referred to by names such as "single use cameras", "lens with film", or "photosensitive material package units".

Another type of color negative element is a color print. Such an element is designed to receive an image optically printed from an image capture color negative element. A color print element may be provided on a reflective support for reflective viewing (e.g. a snap shot) or on a transparent support for projection viewing as in a motion picture. Elements destined for color reflection prints are provided on a reflective support, typically paper, employ silver chloride emulsions, and may be optically printed using the so-called negative-positive process where the element is exposed to light through a color negative film which has been processed as described above. The element is sold with instructions to process using a color negative optical printing process, for example the Kodak RA-4 process, as generally described in PCT WO 87/04534 or U.S. Pat. No. 4,975,357, to form a positive image. Color projection prints may be processed, for example, in accordance with the Kodak ECP-2 process as described in the H-24 Manual. Color print development times are typically 90 seconds or less and desirably 45 or even 30 seconds or less.

A reversal element is capable of forming a positive image without optical printing. To provide a positive (or reversal) image, the color development step is preceded by development with a non-chromogenic developing agent to develop exposed silver halide, but not form dye, and followed by uniformly fogging the element to render unexposed silver halide developable. Such reversal emulsions are typically sold with instructions to process using a color reversal process such as the Kodak E-6 process as described in The British Journal of Photography Annual of 1988, page 194. Alternatively, a direct positive emulsion can be employed to obtain a positive image.

The above elements are typically sold with instructions to process using the appropriate method such as the mentioned color negative (Kodak C-41), color print (Kodak RA-4), or reversal (Kodak E-6) process.

Preferred color developing agents are p-phenylenediamines such as:

4-amino-N,N-diethylaniline hydrochloride, 4-amino-3-methyl-N,N-diethylaniline hydrochloride, 4-amino-3-methyl-N-ethyl-N-(2-methanesulfonamidoethyl)aniline sesquisulfate hydrate, 4-amino-3-methyl-N-ethyl-N-(2-hydroxyethyl)aniline sulfate, 4-amino-3-(2-methanesulfonamidoethyl)-N,N-diethylaniline hydrochloride, and 4-amino-N-ethyl-N-(2-methoxyethyl)-in-toluidine di-p-toluene sulfonic acid.

Development is usually followed by the conventional steps of bleaching, fixing, or bleach-fixing, to remove silver or silver halide, washing, and drying.

The yellow coupler of the invention may be employed, for example in elements comprising the following:

In a color negative element, the materials of the invention may replace or supplement the materials of an element comprising a support bearing the following layers from top to bottom:

(1) one or more overcoat layers containing ultraviolet absorber(s);

(2) a two-coat yellow pack with a fast yellow layer containing "Coup1": Benzoic acid, 4-chloro-3-((2-(4-ethoxy-2,5-dioxo-3-(phenylmethyl)-1-imidazolidinyl)-3-(4-methoxyphenyl)-1,3-dioxopropyl)amino)-, dodecyl ester and a slow yellow layer containing the same compound together with "Coup2": Propanoic acid, 2-[[5-[[4-[2-[[[2,4-bis(1,1-dimethylpropyl)phenoxy]acetyl]amino]-5-[(2,2,3,3,4,4,4-heptafluoro-1-oxobutyl)amino]-4-hydroxyphenoxy]-2,3-dihydroxy-6-[(propylamino)carbonyl ]phenyl]thio]-1,3,4-thiadiazol-2-yl]thio]-, methyl ester and "Coup3": 1-((dodecyloxy)carbonyl) ethyl(3-chloro-4-((3-(2-chloro-4-((1-tridecanoylethoxy) carbonyl)anilino)-3-oxo-2-((4)(5)(6)-(phenoxycarbonyl)-1H-benzotriazol-1-yl)propanoyl)amino))benzoate;

(3) an interlayer containing fine metallic silver;

(4) a triple-coat magenta pack with a fast magenta layer containing "Coup4": Benzamide, 3-((2-(2,4-bis(1,1-dimethylpropyl)phenoxy)-1-oxobutyl)amino)-N-(4,5-dihydro-5-oxo-1-(2,4,6-trichlorophenyl)-1H-pyrazol-3-yl)-,"Coup5": Benzamide, 3-((2-(2,4-bis(1,1-dimethylpropyl)phenoxy)-1-oxobutyl)amino)-N-(4',5'-dihydro-5'-oxo-1'-(2,4,6-trichlorophenyl) (1,4'-bi-1H-pyrazol)-3'-yl)-, "Coup6": Carbamic acid, (6-(((3-(dodecyloxy)propyl) amino)carbonyl)-5-hydroxy-1-naphthalenyl)-, 2-methylpropyl ester, "Coup7": Acetic acid, ((2-((3-(((3-(dodecyloxy)propyl)amino) carbonyl)-4-hydroxy-8-(((2-methylpropoxy)carbonyl) amino)-1-naphthalenyl)oxy )ethyl)thio)-, and "Coup8" Benzamide, 3-((2-(2,4-bis(1,1-dimethylpropyl) phenoxy)-1-oxobutyl)amino)-N-(4,5-dihydro-4-((4-methoxyphenyl) azo)-5-oxo-1-(2,4,6-trichlorophenyl)-1H-pyrazol-3-yl)-; a mid-magenta layer and a slow magenta layer each containing "Coup9": a ternary copolymer containing by weight in the ratio 1:1:2

2-Propenoic acid butyl ester, styrene, and N-[1-(2,4,6-trichlorophenyl)-4,5-dihydro-5-oxo-1H-pyrazol-3-yl]-2-methyl-2-propenamide; and "Coup10": Tetradecanamide, N-(4-chloro-3-((4-((4-((2,2-dimethyl-1-oxopropyl) amino)phenyl)azo)-4,5-dihydro-5-oxo-1-(2,4,6-trichlorophenyl)-1H-pyrazol-3-yl)amino)phenyl)-, in addition to Couplers 3 and 8;

(5) an interlayer;

(6) a triple-coat cyan pack with a fast cyan layer containing Couplers 6 and 7; a mid-cyan containing Coup6 and "Coup 11": 2,7-Naphthalenedisulfonic acid, 5-(acetylamino)-3-((4-(2-((3-(((3-(2,4-bis(1,1-dimethylpropyl)phenoxy) propyl)amino)carbonyl)-4-hydroxy-1-naphthalenyl) oxy)ethoxy)phenyl)azo)-4-hydroxy-, disodium salt; and a slow cyan layer containing Couplers 2 and 6;

(7) an undercoat layer containing Coup8; and (8) an antihalation layer.

In a color paper format, the materials of the invention may replace or supplement the materials of an element comprising a support bearing the following layers from top to bottom:

(1) one or more overcoats;

(2) a cyan layer containing "Coup1": Butanamide, 2-(2,4-bis(1,1-dimethylpropyl)phenoxy)-N-(3,5-dichloro-2-hydroxy-4-methylphenyl)-, "Coup2":Acetamide, 2-(2,4-bis(1,1-dimethylpropyl)phenoxy)-N-(3,5-dichloro-2-hydroxy-4-methylphenyl)-, and UV Stabilizers: Phenol, 2-(5-chloro-2H-benzotriazol-2-yl)-4,6-bis(1,1-dimethylethyl)-;Phenol, 2-(2H-benzotriazol-2-yl)-4-(1,1-dimethylethyl)-;Phenol, 2-(2H-benzotriazol-2-yl)-4-(1,1-dimethylethyl)-6-(1-methylpropyl)-; and Phenol, 2-(2H-benzotriazol-2-yl)-4,6-bis(1,1-dimethylpropyl)- and a poly(t-butylacrylamide) dye stabilizer;

(3) an interlayer;

(4) a magenta layer containing "Coup3": Octanamide, 2-[2,4-bis(1,1-dimethylpropyl)phenoxy]-N-[2-(7-chloro-6-methyl-1H-pyrazolo[1,5-b][1,2,4]triazol-2-yl)propyl]- together with 1,1'-Spirobi(1H-indene), 2,2',3,3'-tetrahydro-3,3,3',3'-tetramethyl-5,5',6,6'-tetrapropoxy-;

(5) an interlayer; and (6) a yellow layer containing "Coup4": 1-Imidazolidineacetamide, N-(5-((2-(2,4-bis(1,1-dimethylpropyl)phenoxy)-1-oxobutyl)amino)-2-chlorophenyl)-.alpha.-(2,2-dimethyl-1-oxopropyl)-4-ethoxy-2,5-dioxo-3-(phenylmethyl)-.

In a reversal format, the materials of the invention may replace or supplement the materials of an element comprising a support bearing the following layers from top to bottom:

(1) one or more overcoat layers;

(2) a nonsensitized silver halide containing layer;

(3) a triple-coat yellow layer pack with a fast yellow layer containing "Coup1": Benzoic acid, 4-(1-(((2-chloro-5-((dodecylsulfonyl)amino)phenyl) amino)carbonyl)-3,3-dimethyl-2-oxobutoxy)-, 1-methylethyl ester; a mid yellow layer containing Coup1 and "Coup2": Benzoic acid, 4-chloro-3-[[2-[4-ethoxy-2,5-dioxo-3-(phenylmethyl)-1-imidazolidinyl]-4,4-dimethyl-1,3-dioxopentyl]amino]-, dodecylester; and a slow yellow layer also containing Coup2;

(4) an interlayer;

(5) a layer of fine-grained silver;

(6) an interlayer;

(7) a triple-coated magenta pack with a fast and mid magenta layer containing "Coup3": 2-Propenoic acid, butyl ester, polymer with N-[1-(2,5-dichlorophenyl)-4,5-dihydro-5-oxo-1H-pyrazol-3-yl]-2-methyl-2-propenamide; "Coup4": Benzamide, 3-((2-(2,4-bis(1,1-dimethylpropyl)phenoxy)-1-oxobutyl)amino)-N-(4,5-dihydro-5-oxo-1-(2,4,6-trichlorophenyl)-1H-pyrazol-3-yl)-; and "Coup5": Benzamide, 3-(((2,4-bis(1,1-dimethylpropyl)phenoxy)acetyl)amino)-N-(4,5-dihydro-5-oxo-1-(2,4,6-trichlorophenyl)-1H-pyrazol-3-yl)-; and containing the stabilizer1,1'-Spirobi(1H-indene), 2,2',3,3'-tetrahydro-3,3,3',3'-tetramethyl-5,5',6,6'-tetrapropoxy-; and in the slow magenta layer Couplers 4 and 5 with the same stabilizer;

(8) one or more interlayers possibly including fine-grained nonsensitized silver halide;

(9) a triple-coated cyan pack with a fast cyan layer containing "Coup6": Tetradecanamide, 2-(2-cyanophenoxy)-N-(4-((2,2,3,3,4,4,4-heptafluoro-1-oxobutyl)amino)-3-hydroxyphenyl)-; a mid cyan containing "Coup7": Butanamide, N-(4-((2-(2,4-bis(1,1-dimethylpropyl)phenoxy)-1-oxobutyl)amino)-2-hydroxyphenyl)-2,2,3,3,4,4,4-heptafluoro- and "Coup8": Hexanamide, 2-( 2,4-bis(1,1-dimethylpropyl)phenoxy)-N-(4-((2,2,3,3,4,4,4-heptafluoro-1-oxobutyl)amino)-3-hydroxyphenyl)-; and a slow cyan layer containing Couplers 6, 7, and 8;

(10) one or more interlayers possibly including fine-grained nonsensitized silver halide; and

(11) an antihalation layer.

Schemes

The couplers of this invention can be prepared from the requisite pyrroles using variations of the methods of Clark, et al., U.S. Pat. No. 5,674,66. A variety of useful pyrroles, in turn, are readily available via literature procedures. Alternatively, compounds can be synthesized as outlined below.

Preparation of a 3-Pyrroloylacetanilide Coupler and Dye

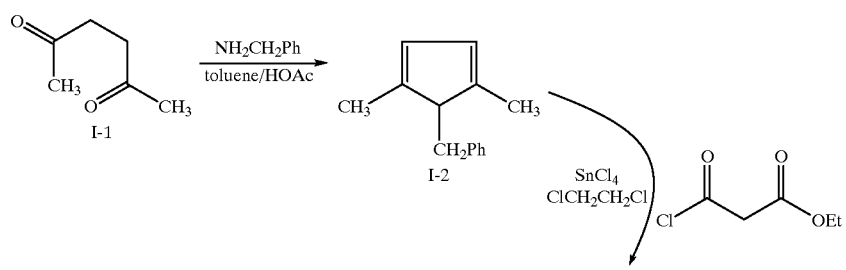

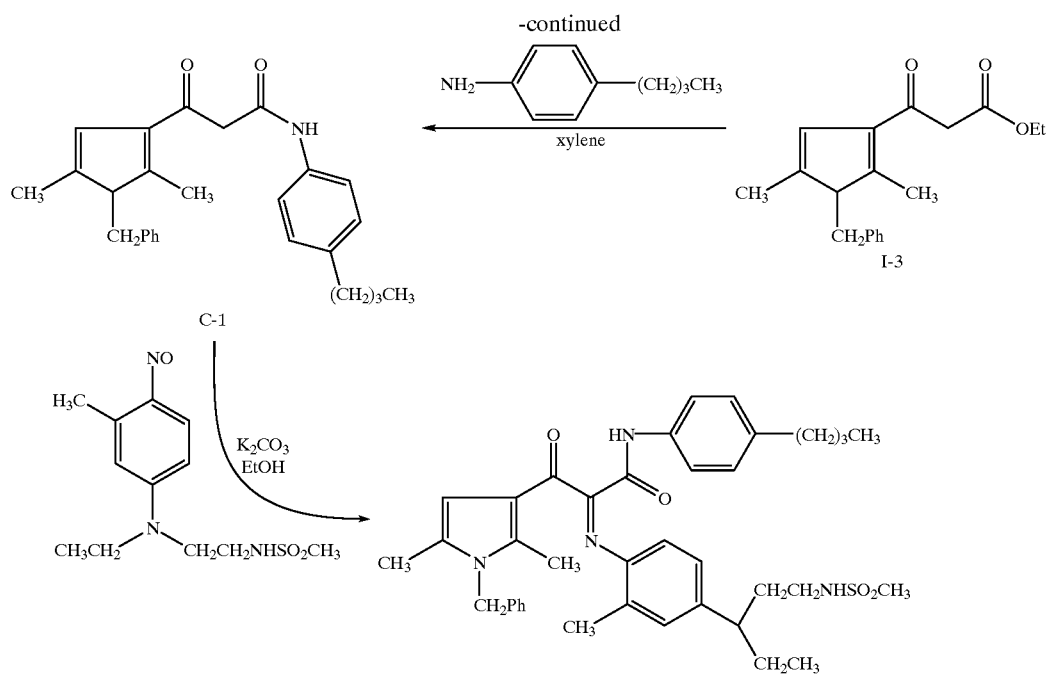

SYNTHETIC EXAMPLES

The following are experimental procedures for the preparation of C-1 and D-1 according to the synthetic scheme depicted above (Scheme). These procedures may also be extended to the preparation of a variety of other pyrrole couplers.

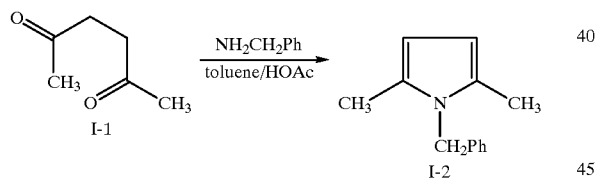

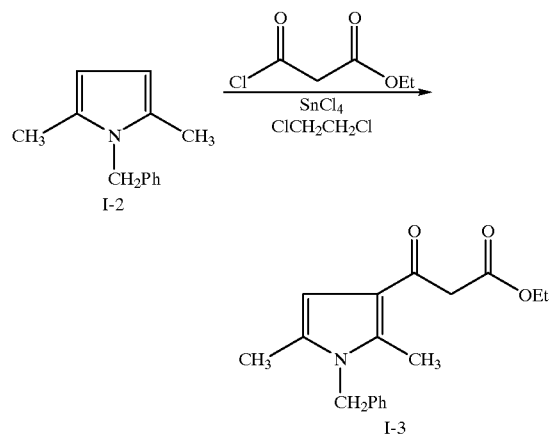

Preparation of 2,5-Dimethyl-1-benzylpyrrole (I-2, a representative 2,5-dimethylpyrrole formation reaction):

A mixture of benzylamine (10.7 g, 0.10 mol) and 2,5-hexanedione (11.4 g, 0.10 mol) and acetic acid (2.5 mL, 0.04 mol) in 50 mL toluene was heated at reflux under a Dean-Stark trap for 0.75hr. The resulting mixture was concentrated in vacuo to provide a viscous oil. The oil was dissolved in several volumes of isopropyl ether, then the solution was washed with 10% aqueous hydrochloric acid. The ether solution was dried and concentrated in vacuo to provide 2,5-dimethyl-1-benzylpyrrole (17.1 g, 92%) as a thick oil which eventually crystallized. The product was chromatographically homogenous and displayed an NMR spectrum consistent with its assigned structure.

Preparation of Ethyl 2,5-Dimethyl-1-benzylindol-3-oyl-acetoacetate (I-3, a representative Friedel-Crafts acylation reaction):

A solution of 2,5-dimethyl-1-benzylpyrrole (I2; 15.7 g, 85 mmol) and ethyl malonyl chloride (Aldrich Chemical Co.; 15.1 g, 85 mmol) in 100 mL 1,2-dichloroethane was treated with stannic chloride (22.3 g, 75 mmol) over 1 min. The mixture stirred 50° C. for 2.5 hr and then at reflux for a further 1 hr. The mixture was cooled briefly then poured onto ice. A dichloromethane extractive work-up provided, after drying and concentration in vacuo, a dark oil. Silica gel chromatography, eluting with dichloromethane, gave ethyl 2,5-dimethyl-1-benzylindol-3-oyl-acetoacetate as a red-brown oil (18.1 g, 71%). The product was chromatographically homogenous and displayed an NMR spectrum consistent with its assigned structure.

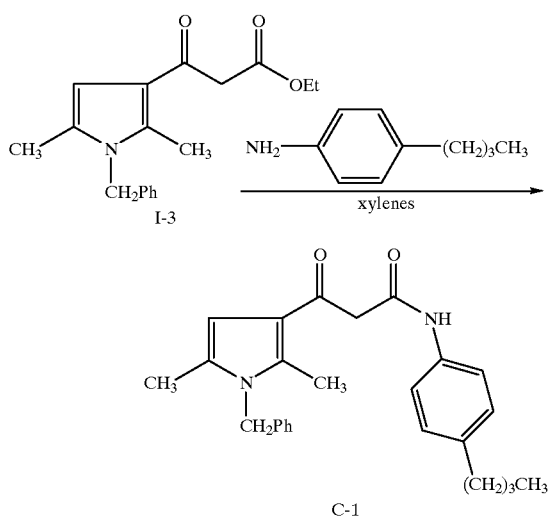

Preparation C-1: (I-3, a representative anilide formation reaction):

A mixture of ethyl 2,5-dimethyl-1-benzylpyrrol-3-oyl-acetoacetate (2.99 g, 10 mmol) and p-butylaniline (Aldrich Chemical Co.; 2.0 g, 13 mmol) in 25 ml xylenes was heated at 150–155° C. under a Dean-Stark trap (refluxing part way up the trap's neck) for 1.5 hr. The mixture was cooled and dissolved in a mixture of ethyl acetate and tetrahydrofuran (THF). The solution was washed with 10% aqueous hydrochloric acid, dried, then concentrated in vacuo. The dark, solid residue was triturated with ca. 50 mL ethyl ether then filtered to afford C-1 as a colorless solid (3.10 g, 77%). The product was chromatographically homogenous and displayed an NMR spectrum consistent with its assigned structure.

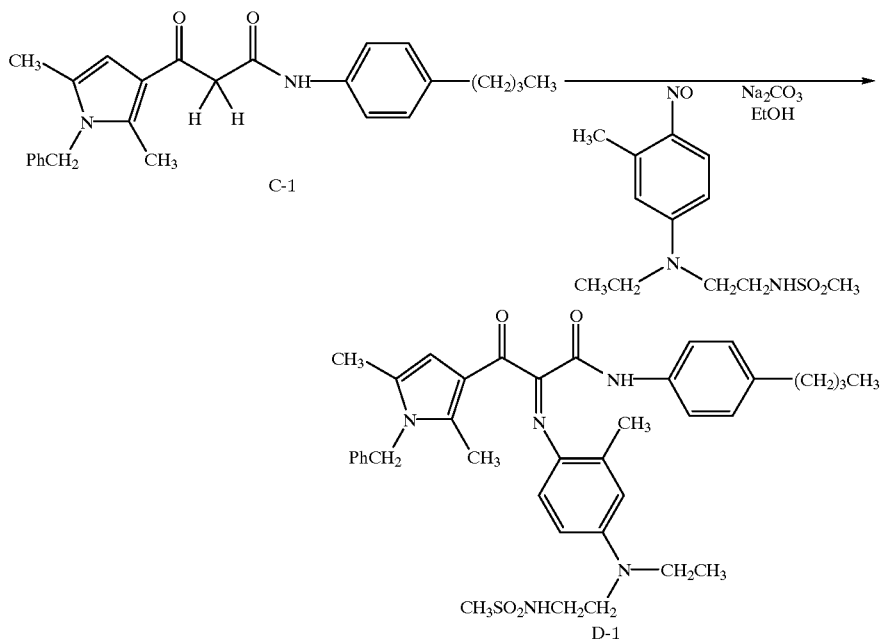

Preparation of D-1 (a representative dye formation reaction):
A mixture of C-1 (0.30 g, 0.75 mmol), 4-(N-(2-methanesulfonamidoethyl)-N-ethylamino)-3-methylnitrosobenzene (0.28 g, 1.0 mmol) and anhydrous potassium carbonate (0.26 g, 2 mmol)) in 25 mL ethanol was heated at reflux for 75 minutes. The mixture was poured into ice water. Extractive ethyl acetate work-up afforded a red oil. This residue was chromatographed on silica gel eluting with mixtures of dichloromethane and ethyl acetate to afford the desired dye, D-1, as a red-orange glass (0.32 g, 64%). The product was chromatographically homogenous and displayed an NMR spectrum consistent with its assigned structure.

PHOTOGRAPHIC EXAMPLES

The following comparative dyes were employed in testing.

TABLE I

Comparative Dyes

Cmp-1

Cmp-2

Cmp-3

A representative series of dyes was prepared; these structures are found in Table II.

TABLE II

Representative Dyes

| Dye Compound | $R^1$ | $R^2$ | $R^4$ | $R^5$ |
|---|---|---|---|---|
| D-1 | $CH_2Ph$ | $CH_3$ | H | $CH_3$ |
| D-2 | Ph | $CH_3$ | H | H |
| D-3 | Ph | $CH_3$ | H | $CH_3$ |
| D-4 | $CH_3$ | Ph | H | Ph |

As mentioned previously, many characteristics of a photographic image depend upon the spectral response of the dyes forming that image. The greater the molar extinction of an image-forming dye the less silver is needed to produce that dye; lower silver laydowns often lead to sharper photographic images. The color of a dye depends upon the position of its maximum light absorption (λ-max). With yellow dyes, the deeper the λ-max of the dye the more orange the color of the dye. Orange dyes cannot be employed to effectively reproduce bright lemon yellows, thus lighter yellow dyes are preferred for better color reproduction. Finally, the ideal yellow dye absorbs only light in the blue portion of the visible spectrum; yellow dyes that absorb substantial amounts of green light appear desaturated and therefore yield poorer color reproduction. The bathochromic one-half bandwidth (B1/2BW) is a good measure of the degree of unwanted absorption of a particular yellow dye. The B1/2BW is the distance on the dye's spectral response curve, in nanometers, from the λ-max to the wavelength of 1/2 the maximum absorption. The smaller the B1/2BW distance, the more sharp-cutting is the spectral response of a dye and the better the color reproduction available from the dye. The spectrophotometric response data for several dyes are summarized in Table III.

TABLE III

Dye Characteristics[a]

| Compound | λ-max nm | Extinction | B1/2BW nm |
|---|---|---|---|
| Cmp-1[b] | 430 | 12,800 | 43 |
| Cmp-2[b] | 428 | 13,900 | 41 |
| Cmp-3[b] | 434 | 12,600 | 40 |
| D-1 | 424 | 14,600 | 38 |
| D-2 | 426 | 13,700 | 40 |
| D-3 | 424 | 14,800 | 38 |
| D-4 | 425 | 16,400 | 35 |

[a]Spectrophotometric data derived from dilute acetonitrile solutions of chromatographically homogenous dyes.
[b]Comparative example from Clark, et al.; See Table I.

These data clearly show that the placement of a substituent onto one of the two positions adjacent to the azole nitrogen, i.e., on carbon-2 or carbon-5 leads to a more lemon colored dye by shifting the λ-max by at least four nanometers; compare Cmp-2 and D-2. This change in substituent position also leads to a sharper-cutting dye hue as the B1/2BW drops. The addition of further substituents leads to improvements in dye hue ( see D-1, D-3 and D-4). The additional substituents afford dyes with even more hypsochromic hues; these dyes also have substantially higher extinctions and smaller B1/2BW's.

The hydrolytic stability of the yellow image dye is an important component of an image's overall stability. The comparison of alkali catalyzed azomethine dye hydrolyses has been used to determine the relative stability of a variety of dyes. The base hydrolysis profiles for a number of dyes have now been explored and the derived data is summarized in Table IV The positioning of a substituent on carbon-2 is shown to be superior to having that substituent on carbon-4; the dye Cmp-2 displays a 39% dye loss while its isomer D-2 shows only a 28% loss. Further improvement in stability is noted with further ring substitution. The dye D-3 showed only a 4% loss under these drastic conditions. These data clearly show that substitution adjacent to the azole nitrogen improve the alkaline stability of these azomethine dyes and that more complete azole substitution leads to further alkaline stability improvements.

TABLE IV

Dye Alkaline Stability

| Compound | % Dye Loss[a] |
|---|---|
| Cmp-1[b] | 70 |
| Cmp-2[b] | 39 |
| Cmp-3[b] | 62 |
| D-1 | 16 |
| D-2 | 28 |
| D-3 | 4 |
| D-4 | 10 |

[a]Percent of dye remaining, as determined by standard HPLC procedures, after 2 h in a 1:1 (v/v) mixture of acetonitrile and aqueous phosphate buffer ($\mu = 0.25$; pH 13.3) at 50 C.
[b]Comparative example from Clark, et al. U.S. 5,674,667.

Multilayer Example:

A multilayer photographic element designed for reversal processing in accordance with Process E-6 of Eastman Kodak Co. provides useful yellow images and is constructed on a gel-subbe acetate support in the following manner. Amounts are in grams per square meter. Laydowns of silver containing components are expressed in grams of silver per square meter.

Layer 1: Antihalation Layer

| | |
|---|---|
| Black colloidal Silver | 0.25 (as silver) |
| UV Dye UV-1 | 0.04 |
| Dispersed in Solvent S-1 | 0.04 |
| Gelatin | 2.44 |

Layer 2: First Interlayer

| | |
|---|---|
| Fine Grain Silver Bromide | 0.05 (as silver) |
| 0.055 μm equivalent spherical diameter | |
| SCV-1 | 0.05 |
| Gelatin | 1.22 |

Layer 3: Low speed Red Sensitive Layer

| | |
|---|---|
| Silver iodobromide emulsion | 0.25 (as silver) |
| 0.50 μm (diameter) by 0.058 μm (thickness) 4% bulk iodide emulsion spectrally sensitized with dyes SD-0 and SD-1 | |
| Fine Grain Silver Bromide | 0.04 (as silver) |
| 0.055 μm equivalent spherical diameter | |
| Cyan Coupler Cy-1 | 0.09 |
| Dispersed in Solvent S-3 | 0.04 |
| Gelatin | 1.08 |

Layer 4: Medium Speed Red Sensitive Layer

| | |
|---|---|
| Silver Iodobromide Emulsion | 0.34 (as silver) |
| 0.88 μm (diameter) by 0.091 μm (thickness) 4% bulk iodide spectrally sensitized with dyes SD-0 and SD-1 | |
| Fine Grain Silver Bromide | 0.05 (as silver) |
| 0.055 μm equivalent spherical diameter | |
| Cyan Coupler Cy-1 | 0.41 |
| Dispersed in Solvent S-3 | 0.20 |
| Gelatin | 0.73 |

Layer 5: High Speed Red Sensitive Layer

| | |
|---|---|
| Silver Iodobromide Emulsion | 0.46 (as silver) |
| 1.11 μm (diameter) by 0.103 μm (thickness) 3% bulk iodide spectrally sensitized with dyes SD-0 and SD-1 | |
| Fine Grain Silver Bromide | 0.03 (as silver) |
| 0.055 μm equivalent spherical diameter | |
| Cyan Coupler Cy-1 | 0.70 |
| Dispersed in Solvent S-3 | 0.35 |
| Gelatin | 1.19 |

Layer 6: Second Interlayer

| | |
|---|---|
| Filter Dye FD-1 | 0.06 |
| Inhibitor I-1 | 0.001 |
| SCV-1 | 0.16 |
| Gelatin | 0.81 |

Layer 7: Third Interlayer

| | |
|---|---|
| Gelatin | 0.61 |

Layer 8: Low Speed Green Sensitive Layer

| | |
|---|---|
| Silver Iodobromide Emulsion | 0.31 (as silver) |
| 0.44 μm (diameter) by 0.057 μm (thickness) 4% bulk iodide spectrally sensitized with dyes SD-4 and SD-5 | |
| Fine Grain Silver Bromide | 0.04 (as silver) |
| 0.055 μm equivalent spherical diameter | |
| Magenta Coupler M-1 | 0.07 |
| Magenta Coupler M-2 | 0.03 |
| co-dispersed in Solvent S-2 | 0.05 |
| Gelatin | 0.47 |

Layer 9: Medium Speed Green Sensitive Layer

| | |
|---|---|
| Silver Iodobromide Emulsion | 0.38 (as silver) |
| 0.64 μm (diameter) by 0.105 μm (thickness) 3% bulk iodide spectrally sensitized with dyes SD-4 and SD-5 | |
| Fogged silver Iodobromide Emulsion | 0.0005 (as silver) |
| Magenta Coupler M-1 | 0.34 |
| Magenta Coupler M-2 | 0.15 |
| Co-dispersed in Solvent S-2 | 0.25 |
| Gelatin | 0.91 |

43

-continued

| Layer 10: High Speed Green Sensitive Layer | |
|---|---|
| Silver Iodobromide Emulsion | 0.54 (as silver) |
| 1.26 μm (diameter) by 0.137 μm (thickness) | |
| 3% bulk iodide | |
| spectrally sensitized with dyes SD-4 and SD-5 | |
| Magenta Coupler M-1 | 0.72 |
| Magenta Coupler M-2 | 0.31 |
| Co-dispersed in Solvent S-2 | 0.52 |
| Gelatin | 1.78 |
| Layer 11: Fourth Interlayer | |
| Gelatin | 0.61 |
| Layer 12: Fifth Interlayer | |
| Carey Lea Silver | 0.07 (as silver) |
| SCV-1 | 0.11 |
| Gelatin | 0.68 |
| Layer 13: Sixth Interlayer | |
| SCV-1 | 0.05 |
| Gelatin | 1.22 |
| Layer 14: Low Speed Blue Sensitive Layer | |
| Silver Iodobromide Emulsion | 0.22 (as silver) |
| 1.04 μm (diameter) by 0.125 μm (thickness) | |
| 3% bulk iodide | |
| spectrally sensitized with dyes SD-6 and SD-7 | |
| Silver Iodobromide Emulsion | 0.15 (as silver) |
| 0.50 μm (diameter) by 0.130 μm (thickness) | |
| 3% bulk iodide | |
| spectrally sensitized with dyes SD-6 and SD-7 | |
| Yellow Coupler of Formula A or B | 0.4–.9 |
| Dispersed in Solvent S-3 | 0.25–0.90 |
| Gelatin | 1.23 |

44

-continued

| Layer 15: High Speed Blue Sensitive Layer | |
|---|---|
| Silver Iodobromide Emulsion | 0.67 (as silver) |
| 2.59 μm (diameter) by 0.154 μm (thickness) | |
| 2% bulk iodide | |
| spectrally sensitized with dyes SD-6 and SD-7 | |
| Yellow Coupler of Formula A or B | 0.5–1.80 |
| Dispersed in Solvent S-3 | 0.51 |
| PC-1 | 0.02 |
| Gelatin | 2.03 |
| Layer 16: First Overcoat | |
| SCV-1 | 0.07 |
| UV Dye UV4 | 0.41 |
| UV Dye UV-1 | 0.09 |
| Dispersed in Latex L-1 | 0.45 |
| PC-1 | 0.06 |
| Gelatin | 1.40 |
| Layer 17: Second Overcoat | |
| Fine Grain Silver Bromide | 0.12 (as silver) |
| 0.055 μm equivalent spherical diameter | |
| Matte | 0.02 |
| 3.3 μ spherical diameter | |
| Hardener H-1 | 1.38% of total gel |
| Gelatin | 0.97 |

The exposed strips were processed in the standard E-6 process.

The components employed for the preparation of light-sensitive materials not already identified above are shown below:

Cy-1

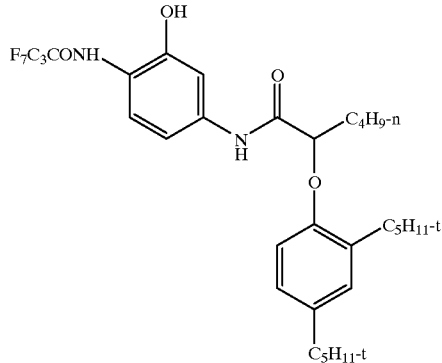

FD-1

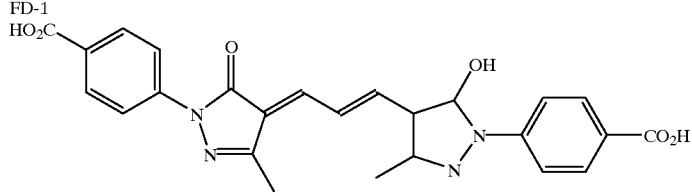

H-1: 1,1'-[methylenebis(sulfonyl)]bis-ethene

I-1

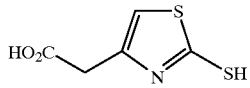

L-1:
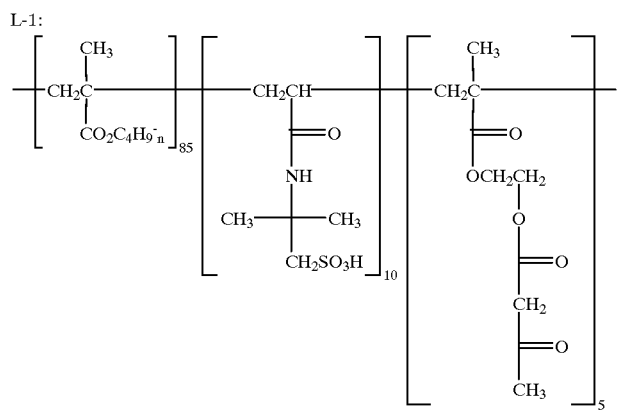
M-1:
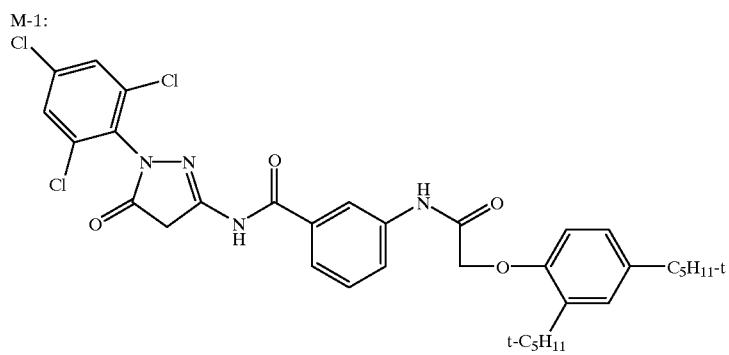
M-2:
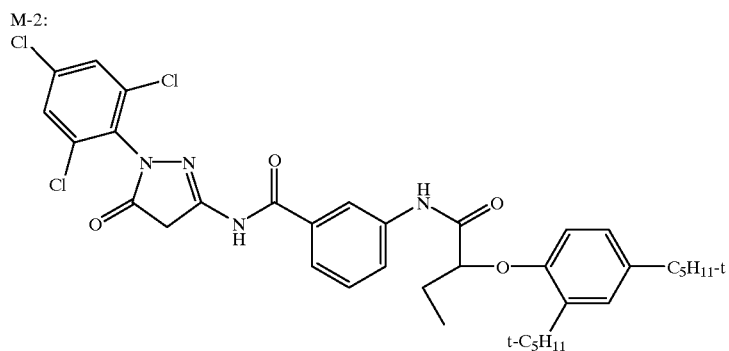
PC-1
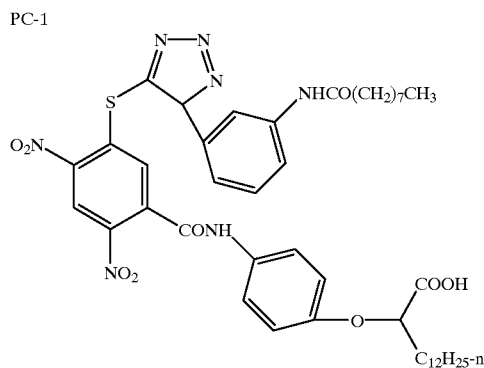
S-1  1,4-Cyclohexylenedimethylene bis(2-ethylhexanoate)

-continued
S-2  Phosphoric Acid, tris(methylphenyl)ester
S-3  1,2-benzenedicarboxylic acid, dibutyl ester
SD-0:
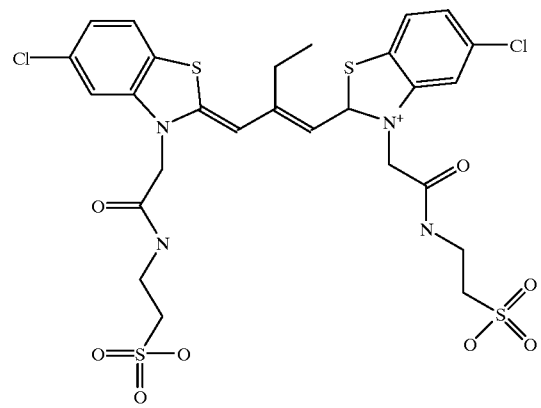
SCV-1:
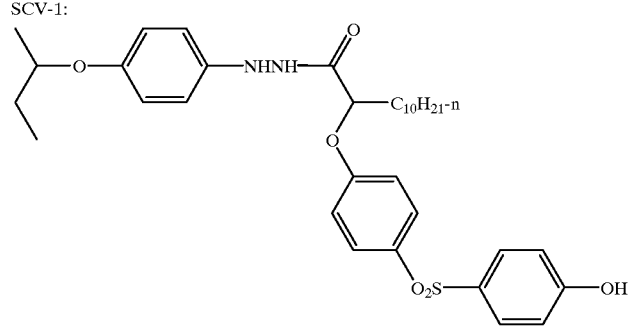
SD-1:
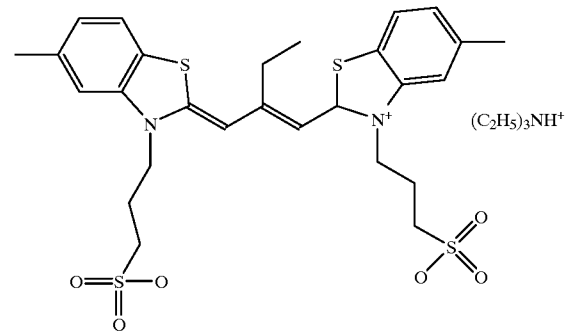
SD-2
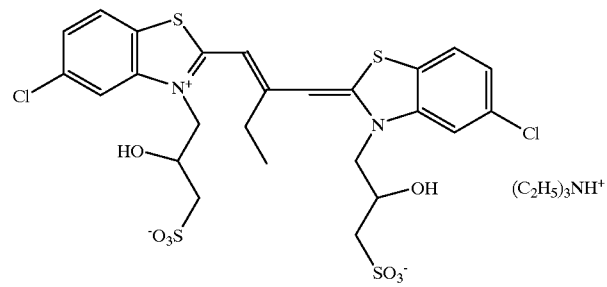

-continued
SD-3:
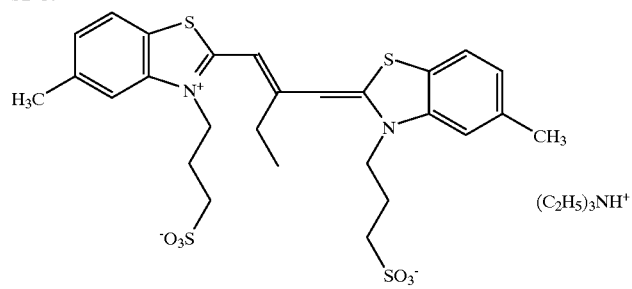
SD-4:
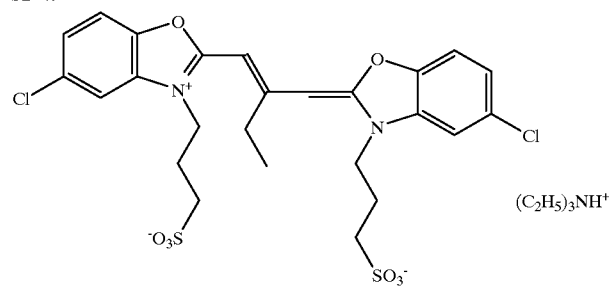
SD-5:
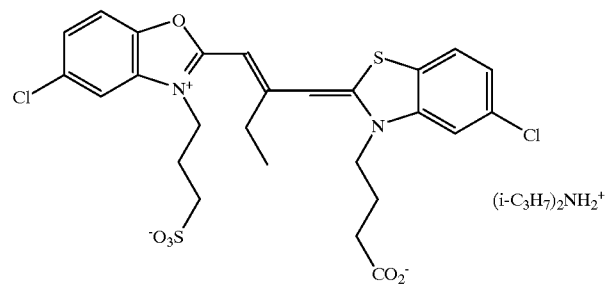
SD-6:
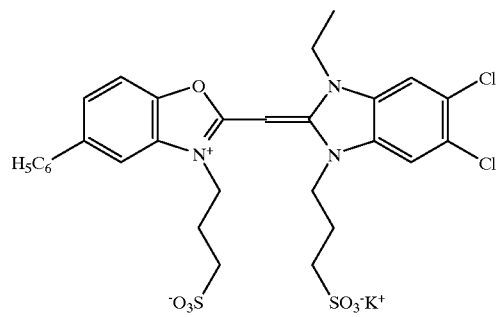
SD-7:
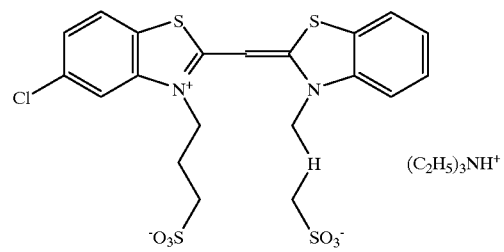

SD-8:
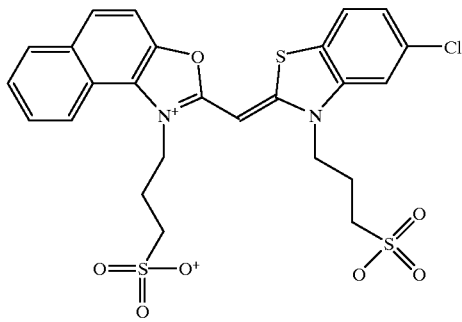

UV-1:
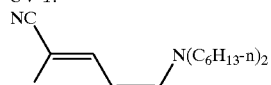

UV-4
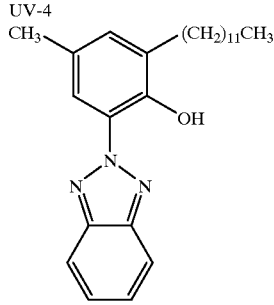

The entire contents of the patent applications, patents and other publications referred to in this specification are incorporated herein by reference.

What is claimed is:

1. A photographic element comprising a silver halide emulsion layer having associated therewith a dye-forming coupler having Formula 1

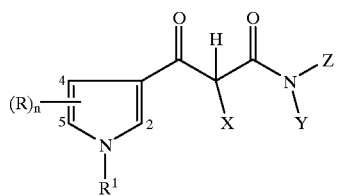

wherein:
X is hydrogen or a coupling-off group, and Y and Z are independently selected hydrogen or a substituent;
$R^1$ is a substituent; and
each R is an independently selected substituent with at least one R substituent located in the 2- or 5-position, and n is 1 to 3;
provided that substituents may join to form a ring.

2. The element of claim 1 wherein $R^1$ is an alkyl or aromatic group.

3. The element of claim 2 wherein $R^1$ is an alkyl group.

4. The element of claim 1 wherein n is at least two and at least two R substituent groups are phenyl groups.

5. The element of claim 1 wherein $R^1$ is selected from the group consisting of alkyl, aryl, and heterocyclic groups.

6. The element of claim 1 wherein an R substituent and $R^1$ join to form a carbocyclic or heterocyclic ring.

7. The element of claim 1 wherein the substituent $R^1$ and an R substituent in the 2- or 5-position of the azole ring join to form a ring.

8. The element of claim 1 wherein $R^1$ joins with an R substituent to form a thiazole or imidazole ring.

9. The element of claim 1 wherein each R is selected from the group consistent of alkyl, acyl, halogen, carboxyl, alkoxy, carbonamido, carbamoyl, heterocyclic, and aryl groups.

10. The element of claim 9 wherein the ring is a thiazole ring.

11. The element of claim 9 wherein the ring is unsaturated.

12. The element of claim 1 wherein X is a halogen or linked to the coupling site of the coupler by an atom of oxygen, sulfur, or nitrogen.

13. The element of claim 12 wherein X is a nitrogen containing heterocycle.

14. The element of claim 1 wherein X is selected from the group consisting of a hydrogen atom, a chlorine atom, and an N-heterocyclic, phenoxy, and phenylthio group.

15. The element of claim 1 wherein Z is H.

16. The element of claim 15 wherein Y is a phenyl group.

17. The element of claim 16 wherein

is represented by the formula:

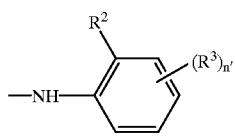

wherein $R^2$ is halogen or alkoxy, each $R^3$ is an independently selected substituent and n' is 1–4.

18. The element of claim 17 wherein n is at least 1 and at least one $R^3$ is a group having a Hammett's sigma value for its location relative to the anilino nitrogen greater than 0.

19. The element of claim 1 wherein the coupler of formula 1 has formula A:

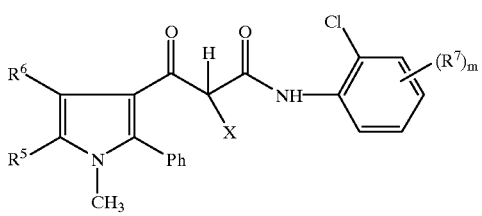

in which $R^5$ and $R^6$ are independently selected hydrogen or substituents, suitably hydrogen or alkyl or aryl groups;

X is hydrogen or a coupling-off group;

each $R^7$ is a substituent and m is 0–4;

provided that substituents may join to form a ring.

20. The element of claim 1 wherein the coupler of formula 1 has formula B:

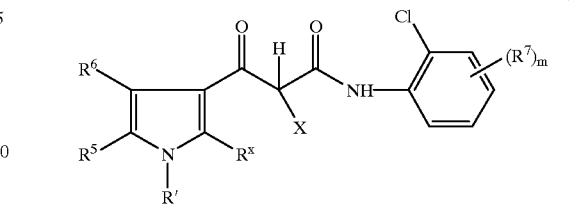

in which $R^5$ and $R^6$ are independently selected hydrogen or substituents, suitably hydrogen or alkyl or aryl groups;

X is hydrogen or a coupling-off group;

R' and $R^x$ are independently selected substituents such as alkyl or aryl groups;

each $R^7$ is a substituent and m is 0–4;

provided that substituents may join to form a ring.

21. A method of forming an image in an element as described in claim 1 after imagewise exposure to light comprising contacting the element with a color developing chemical.

22. A reversal method as described in claim 21 in which the element is subjected to a contact with a black and white developer prior to contact with the color developer in order to form a positive image.

* * * * *